(12) United States Patent
Fesmire et al.

(10) Patent No.: US 9,678,025 B1
(45) Date of Patent: Jun. 13, 2017

(54) GUARDED FLAT PLATE CRYOGENIC TEST APPARATUS AND CALORIMETER

(71) Applicant: The United States of America as Represented by the Administrator of the National Aeronautics and Space Administration, Washington, DC (US)

(72) Inventors: James E. Fesmire, Titusville, FL (US); Wesley L. Johnson, Titusville, FL (US)

(73) Assignee: The United States of America as Represented by the Administrator of the National Aeronautics and Space Administration, Washington, DC (US)

( * ) Notice: Subject to any disclaimer, the term of this patent is extended or adjusted under 35 U.S.C. 154(b) by 554 days.

(21) Appl. No.: 14/199,768

(22) Filed: Mar. 6, 2014

Related U.S. Application Data

(60) Continuation-in-part of application No. 14/090,193, filed on Nov. 26, 2013, now Pat. No. 9,488,607, which is a division of application No. 12/813,864, filed on Jun. 11, 2010, now Pat. No. 8,628,238.

(60) Provisional application No. 61/775,003, filed on Mar. 8, 2013, provisional application No. 61/775,124, filed on Mar. 8, 2013, provisional application No. 61/186,475, filed on Jun. 12, 2009.

(51) Int. Cl.
*G01N 25/72* (2006.01)

(52) U.S. Cl.
CPC .................................. *G01N 25/72* (2013.01)

(58) Field of Classification Search
CPC ........ G01N 25/72; G01N 25/00; G01N 25/02; G01N 25/08; G01N 25/10; G01N 25/145; G01N 25/20; G01N 25/32; G01N 25/4826; G01N 25/484; G01N 25/56; G01N 25/66; G01N 25/68; G01N 27/20; G01N 27/205
USPC .................................................. 374/5, 31, 42
See application file for complete search history.

(56) References Cited

U.S. PATENT DOCUMENTS

| | | | |
|---|---|---|---|
| 3,782,128 A | 1/1974 | Hampton et al. | |
| 4,350,017 A | 9/1982 | Kneip et al. | |
| 4,484,823 A * | 11/1984 | Peuker | G01N 25/08 374/27 |
| 4,762,423 A * | 8/1988 | Basta | G01K 17/025 374/31 |
| 5,339,650 A | 8/1994 | Hakamada et al. | |
| 5,484,204 A * | 1/1996 | Damley | G01N 25/4826 374/10 |

(Continued)

*Primary Examiner* — Michael A Lyons
*Assistant Examiner* — Philip Cotey
(74) *Attorney, Agent, or Firm* — Michelle L. Ford; David E. Franklin

(57) ABSTRACT

A test apparatus for thermal energy measurement of disk-shaped test specimens has a cold mass assembly locatable within a sealable chamber with a guard vessel having a guard chamber to receive a liquid fluid and a bottom surface to contact a cold side of a test specimen, and a test vessel having a test chamber to receive a liquid fluid and encompassed on one side by a center portion of the bottom surface shared with the guard vessel. A lateral wall assembly of the test vessel is closed by a vessel top, the lateral wall assembly comprising an outer wall and an inner wall having opposing surfaces that define a thermal break including a condensable vapor pocket to inhibit heat transfer through the lateral wall from the guard vessel to the test vessel. A warm boundary temperature surface is in thermal communication with a lower surface of the test specimen.

13 Claims, 23 Drawing Sheets

(56) References Cited

U.S. PATENT DOCUMENTS

| | | |
|---|---|---|
| 6,487,866 B1 | 12/2002 | Fesmire et al. |
| 6,742,926 B1 | 6/2004 | Fesmire et al. |
| 6,824,306 B1 | 11/2004 | Fesmire |
| 7,540,656 B1 | 6/2009 | Stochl et al. |
| 8,628,238 B2 | 1/2014 | Fesmire et al. |
| 2005/0213633 A1* | 9/2005 | Burian .................. G01N 25/08 374/27 |
| 2006/0251145 A1* | 11/2006 | Brushwyler ........... G01K 17/00 374/31 |
| 2008/0304542 A1* | 12/2008 | Danley .................. G01K 17/00 374/31 |
| 2009/0092170 A1 | 4/2009 | Brushwyler et al. |
| 2010/0318316 A1* | 12/2010 | Fesmire ................ G01K 17/00 702/136 |

\* cited by examiner

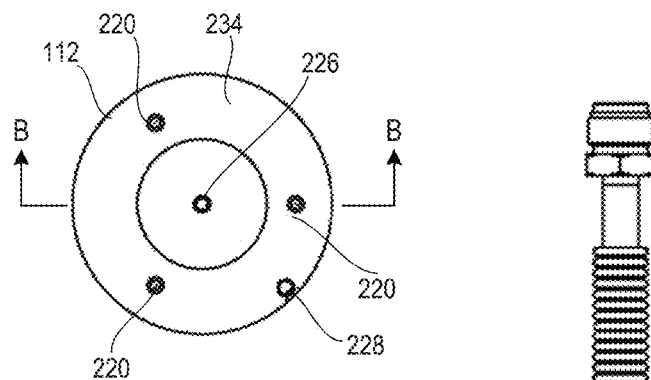
FIG. 10
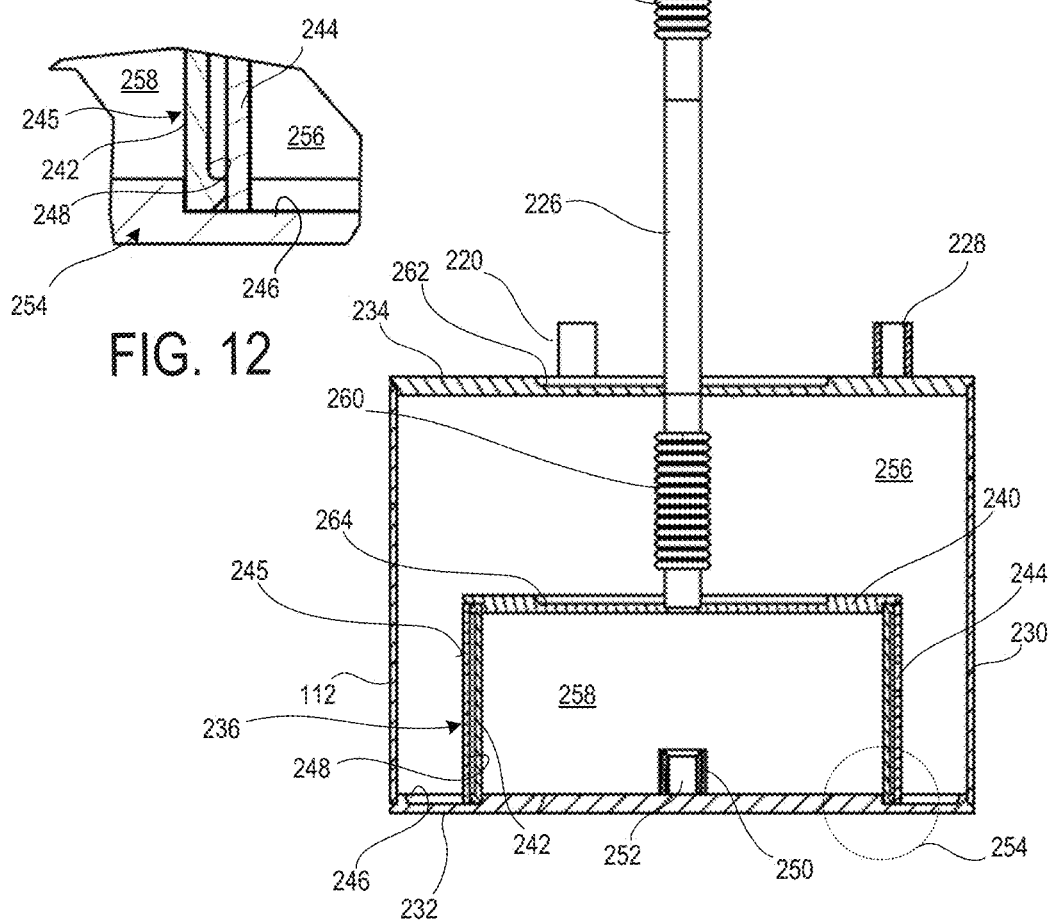
FIG. 12
FIG. 11

GUARDED FLAT PLATE CRYOGENIC TEST APPARATUS AND CALORIMETER

CROSS-REFERENCE TO RELATED APPLICATIONS

This application claims the benefit of priority under 35 U.S.C. §119(e) to U.S. Provisional Application Ser. No. 61/775,003 entitled "Guarded Flat Plate Insulation Test Apparatus (Cryostat-500)" and to U.S. Provisional Application Ser. No. 61/775,124 entitled "Guarded Two Dimensional Flat Plate calorimeter (Cryostat-600)" both filed on Mar. 8, 2013, the contents of which are incorporated herein by reference in their entirety. This application is a continuation-in-part of U.S. patent application Ser. No. 14/090,193, filed on Nov. 26, 2013, which issued as U.S. Pat. No. 9,488,607 on Nov. 8, 2016, which in turn is a divisional application of U.S. patent application Ser. No. 12/813,864 filed on Jun. 11, 2010, which issued as U.S. Pat. No. 8,628,238 on Jan. 14, 2014, and which further claims the benefit of priority under 35 U.S.C. §119(e) to U.S. Provisional Application Ser. No. 61/186,475 filed Jun. 12, 2009, the contents of which are incorporated herein by reference.

ORIGIN OF THE INVENTION

The invention described herein was made by employees of the United States Government and may be manufactured and used by or for the Government of the United States of America for governmental purposes without the payment of any royalties thereon or therefore.

BACKGROUND OF THE INVENTION

1. Technical Field

The present disclosure generally relates to testing apparatus and methods of making precise thermal performance measurements of thermal insulation specimens, and more specifically to testing specimens across a wide range of pressures and temperatures.

2. Description of the Related Art

In today's world of increasing demands for energy and energy efficiency, the use of cryogenics and refrigeration is taking on a more and more significant role in areas including transportation, building construction, electrical power, manufacturing, food processing, pharmaceuticals, and others. To protect storage tanks, transfer lines, and other process system equipment from heat energy, high-performance materials are needed to provide effective thermal insulation to a degree that can be reasonably obtained. Complete and accurate thermal characterization of the insulation material or structural component (e.g., performance attributes of the material such as thermal conductivity and heat flux) are key aspects in designing efficient and effective low-maintenance systems and devices for sub-ambient temperature applications such as refrigeration and cryogenics.

BRIEF SUMMARY OF THE INVENTION

In one aspect, the present disclosure provides a test apparatus for evaporation or boiloff flow measuring to determine thermal performance of a test specimen. The test apparatus has a sealable chamber. The test apparatus also includes a cold mass assembly locatable within the sealable chamber. The cold mass assembly includes a guard vessel having a guard chamber to receive a liquid fluid and a bottom surface to contact a cold side of a test specimen, and a test vessel having a test chamber to receive a liquid fluid and encompassed on one side by a center portion of the bottom surface shared with the guard vessel. The test vessel further has a lateral wall assembly closed by a vessel top. The lateral wall assembly has an outer wall and an inner wall having opposing surfaces that define a thermal break including a condensable vapor pocket to inhibit heat transfer through the lateral wall from the guard vessel to the test vessel. Liquid passages are in communication with the guard vessel and the test vessel to supply the liquid fluid and to vent evaporation or boiloff from the liquid fluid. A warm boundary temperature surface is in thermal communication with a lower surface of the test specimen.

In another aspect, the present disclosure provides a test apparatus for evaporation or boiloff flow measuring to determine thermal performance of a test specimen. The test apparatus includes a sealable chamber and a cold mass assembly locatable within the sealable chamber. The cold mass assembly includes a guard vessel having a guard chamber to receive a liquid fluid and a bottom surface to contact a cold side of a test specimen, and a test vessel having a test chamber to receive a liquid fluid and encompassed on one side by a center portion of the bottom surface shared with the guard vessel. The test vessel further has a lateral wall assembly closed by a vessel top. One or more penetration components are attachable to the bottom surface to pass through the cold side and a warm side of the test specimen. Liquid passages are in communication with the guard vessel and the test vessel to supply the liquid fluid and to vent evaporation or boiloff from the liquid fluid. A heater is within the sealable chamber to warm a portion of space inside the sealable chamber that is occupied by the one or more penetration components and presented to the warm side of the test specimen.

In an additional aspect, the present disclosure provides a test apparatus for evaporation or boiloff flow measuring to determine thermal performance of a test specimen. The test apparatus includes a sealable chamber and a cold mass assembly locatable within the sealable chamber. The cold mass assembly includes a guard vessel having a guard chamber to receive a liquid fluid and a bottom surface to contact a cold side of a test specimen, and a test vessel having a test chamber to receive a liquid fluid and encompassed on one side by a center portion of the bottom surface shared with the guard vessel. The test vessel includes a lateral wall assembly closed by a vessel top. Liquid passages are in communication with the guard vessel and the test vessel to supply the liquid fluid and to vent evaporation or boiloff from the liquid fluid. A warm boundary temperature surface is in thermal communication with a lower surface of the test specimen. A cold edge guard laterally encompasses an outer, lateral edge of the test specimen. The present invention is a flat plate boiloff calorimeter test instrument for measuring the absolute thermal performance of an insulation test specimen. Temperature sensors are located on the cold-mass assembly and through the thickness of the insulation test specimen in addition to the boundary temperatures. System insulation materials within the sealable chamber provide additional thermal stability for testing over a wide range of environmental conditions. The cold-mass assembly can be configured for rigid or soft materials, with or without compressive loads.

The above summary contains simplifications, generalizations, and omissions of detail and is not intended as a comprehensive description of the claimed subject matter but, rather, is intended to provide a brief overview of some of the functionality associated therewith. Other systems, methods, functionality, features, and advantages of the claimed subject matter will be or will become apparent to one with skill in the art upon examination of the following figures and detailed written description.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which:

FIG. 10 illustrates a top view of the cold mass assembly of FIG. 8, according to one embodiment;

FIG. 11 illustrates a side view of the cold mass assembly of FIG. 10 in cross section along lines B-B, according to one embodiment;

FIG. 12 illustrates a detail side view in cross section of the cold mass assembly of FIG. 11;

DETAILED DESCRIPTION OF THE INVENTION

Figure 1:
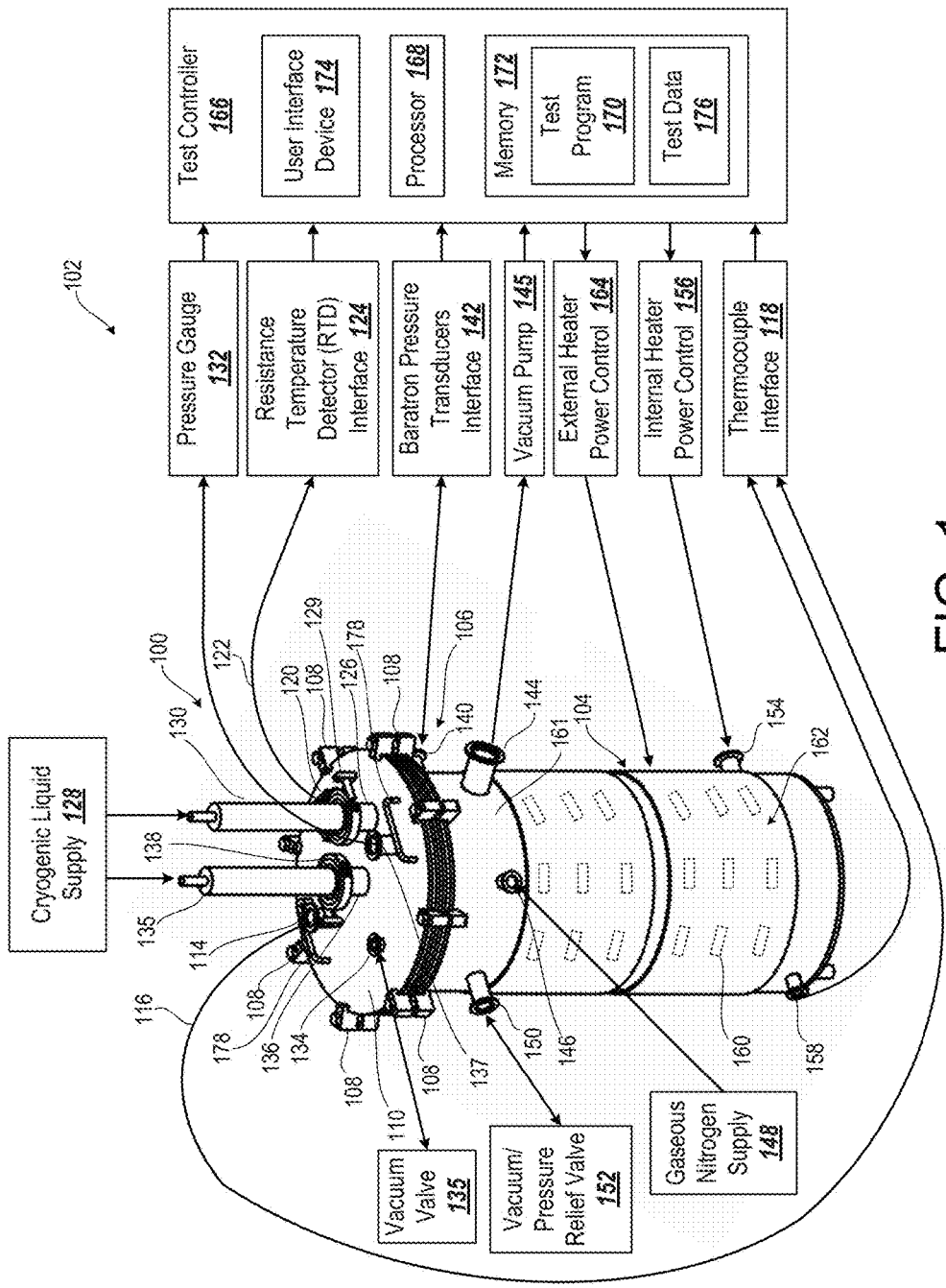
FIG. 1 illustrates an isometric view of a Cryostat-500 assembly and a functional block diagram of a testing system, according to one embodiment.

There exists a basic need for thermal performance data on insulation materials and systems that operate at below ambient temperatures. This need is driven by increasing demand for cryogenic applications in electrical power, energy storage, ground and air transportation, as well as medical imaging, food processing, electronics manufacturing, and space launch and exploration. The performance requirements are also increasing due to steadily increasing demands through energy-efficiency standards in building construction, refrigeration systems, and all energy-related sectors of business and commerce.

One technique for testing the thermal performance of materials, such as insulation material, is evaporation or boiloff testing. Such testing may be accomplished by filling a vessel with a fluid which evaporates or boils below ambient temperature. A vessel is surrounded with the testing material, placed in a suitable environmental chamber, and filled with the test fluid such as a cryogenic liquid. A calorimetric method is used to determine the thermal conductivity of the test material by first determining the rate of heat passing through the test material to the vessel containing the refrigerant liquid. The heat leakage rate passing through the test material to the liquid in the vessel is directly proportional to the liquid boiloff rate from the vessel. For a specific test material under a set vacuum pressure, the effective thermal conductivity ($k_e$) and/or heat flux is determined by measuring the flow rate of boil off at prescribed warm and cold boundary temperatures across the thickness of the sample. The apparatus capable of testing cylindrical samples is more fully described in U.S. Pat. No. 8,628,238 issued on Jan. 14, 2014, and U.S. Patent Application Publication No. US 2010/0318316 published on Dec. 16, 2010, Ser. No. 12/813,864, and incorporated by reference into this application (hereinafter referred as "Cryostat-100 assembly").

A further related invention directed to a test apparatus and method for evaluating various performance aspects of a test specimen is disclosed in U.S. Pat. No. 6,824,306 issued on Nov. 30, 2004, and incorporated by reference into the present application (hereinafter referred to as "Cryostat-400 assembly"). While the Cryostat-100 assembly provided absolute data, it required a relatively large cylindrically-shaped specimen that may not have been available or not representative of the desired insulation system application. The Cryostat-400 assembly allowed a conveniently sized specimen around 200-mm diameter, but provides comparative data that must be further referenced or calibrated against a standard reference material.

As will be described below, the present invention evolved from the Cryostat-100 assembly (cylindrical, absolute boiloff calorimeter) and the Cryostat-400 assembly (flat plate, comparative boiloff calorimeter). In one embodiment, the present invention discloses an insulation testing apparatus, hereinafter referred to as Cryostat-500 assembly, which allows for the testing of conveniently sized and shaped insulative materials by providing a direct route for obtaining absolute thermal conductivity and heat flux test data.

With regard to the Cryostat-500 assembly, the current technology described as the Cryostat-100 assembly and Cryostat-400 assembly do not completely meet all of the new demands listed above. The present invention is complementary, in part, to existing commercial instruments (i.e., ASTM C177 Guarded Hot Plate) but goes far beyond the existing standards in regard to both precision for very low thermal conductivity conditions, as well as achieving the practicality of testing under representative cryogenic and vacuum conditions. Finally, as will become apparent, the Cryostat-500 assembly provides a cost-effective way to obtain precision data on high-performance materials under actual-use conditions.

In one aspect, the Cryostat-500 assembly introduced improvements especially regarding the cold mass design for testing disk shaped test articles of about 8" in diameter. Then, another embodiment of the cold mass design was developed that provided a strut option for testing penetrations through a disk-shaped test specimen. This embodiment referred to as Cryostat-600 also provided for larger test specimens of about 12" in diameter. Thus, Cryostat-600 may specifically refer to changes in the cold mass design; however, the overall test apparatus incorporates the vacuum canister previously referenced and incorporated for the Cryostat-100 (Ser. No. 12/813,864). For clarity, the overall test apparatus that incorporates the innovative cold mass for testing a strut penetration is referred to as the Cryostat-600 assembly.

With regard to the Cryostat-600 assembly, it should be appreciated that insulation systems never operate on their own. They must work together within a structural system that is designed to support the article being insulated. It is necessary that the structure go through the insulation, degrading it in some manner. High-performance insulation systems that use reflective foils are highly anisotropic (heat flows more easily in one direction than the other), thus disturbing the temperature gradients throughout the material can cause much greater effects than are caused by the disturbances alone. A method and apparatus is needed to measure the degradation of such structural, electrical and fluid supports to give better thermal performance predictions for the results in both extraterrestrial or space-based systems and ground systems.

In the following detailed description of exemplary embodiments of the disclosure, specific exemplary embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. It is also to be understood that other embodiments may be utilized and that logical, architectural, programmatic, mechanical, electrical and other changes may be made without departing from the general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments," or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not other embodiments.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that terms is utilized.

In FIGS. 1-16, a Cryostat-500 (C-500) assembly 100 provides a wide range of heat-flux performance over the full range of environmental conditions including vacuum levels from 10E−7 to 10E+3 torr. The C-500 assembly 100 has been successfully proven through extensive testing of multilayer insulation (MLI) systems, aerogel blankets, fiberglass, foams, composites, structural panels, etc. Both the quantity and quality of thermal testing data for insulation materials and systems have increased even as the process and method has become more time efficient and cost effective.

Figure 3:
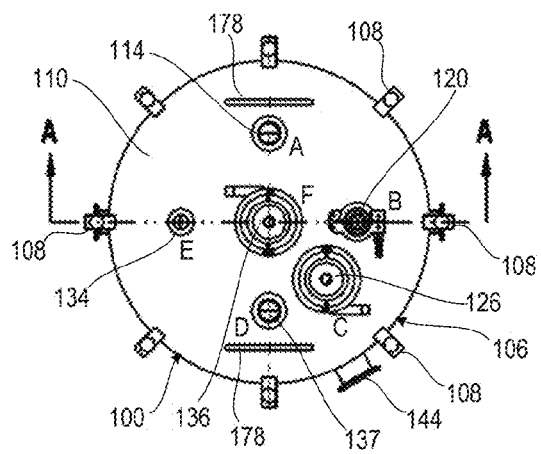
FIG. 3 illustrates a top view of the Cryostat-500 assembly of FIG. 2, according to one embodiment.
Figure 2:
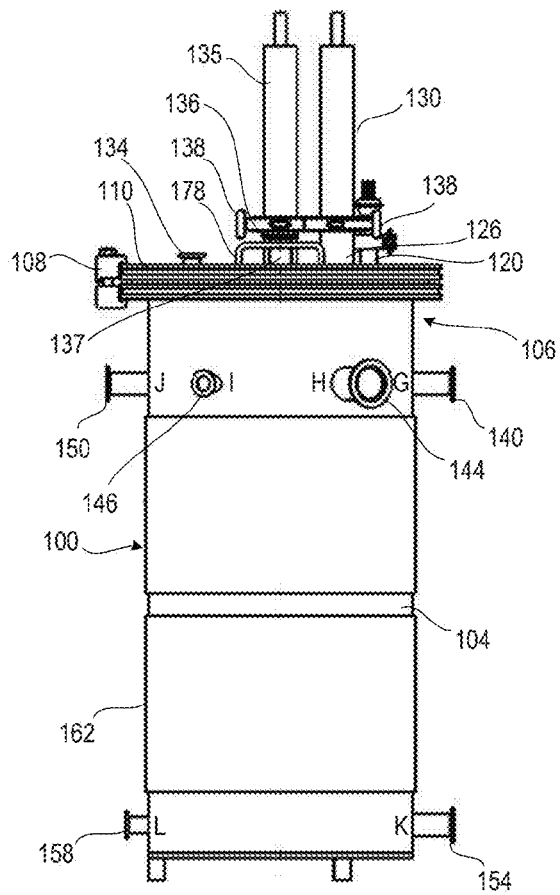
FIG. 2 illustrates a side view of a Cryostat-500 assembly of the testing system, according to one embodiment.

With particular reference to FIG. 1-3, the C-500 assembly 100 of a cryogenic testing system 102 includes a vacuum chamber can 104 having vacuum chamber lid assembly 106 overtop and clamped to it in a sealed state by eight (8) chamber lid clamps 108. Ports A-F pass through a vacuum chamber lid 110 of the vacuum chamber lid assembly 106 and ports G-L pass through vacuum chamber can 104 that contains a cold mass vessel 112 (FIG. 4):

Port A 114 is a 25 mm diameter opening that provides a thermocouple feedthrough 116 in electrical communication with a thermocouple interface 118;

Port B 120 is a 16 mm diameter opening that receives a resistance temperature detector (RTD) feedthrough 122 in electrical communication with an RTD interface 124;

Port C 126 is a 40 mm diameter opening that receives a cryogenic liquid such as liquid nitrogen (LN2) from a LN2 supply 128 via an upper LN2 feedthrough 130 attached to Port C 126 by an LN2 feedthrough clamp 129;

Port D 137 is a 25 mm diameter opening that is pneumatic communication with a pressure gage 132;

Port E 134 is a 16 mm diameter opening that is pneumatic communication with a vacuum valve 135;

Port F 136 is a 40 mm diameter that is in fluid communication with the LN2 supply 128 via another upper LN2 feedthrough 135 and attached to Port F 136 by another LN2 feedthrough clamp 138;

Port G 140 is a 25 mm diameter opening for baratron pressure transducers to be electrical communication with a Baratron capacitance manometer pressure transducers interface 142;

Port H 144 is a 40 mm diameter opening that is in pneumatic communication with a vacuum pump (turbo) 145;

Port I 146 is a 16 mm diameter opening that is in pneumatic communication with a gaseous nitrogen (GN2) supply 148;

Port J 150 is a 25 mm diameter that is in pneumatic communication with a vacuum/pressure relief valve 152;

Port K 154 is a 25 mm diameter opening that serves as a power feedthrough in electrical communication with an internal heater power control 156; and Port L 158 is a 16 mm diameter opening that serves as a thermocouple feedthrough in electrical communication with the thermocouple interface 118.

More than one flexible heating element 160 is positioned on an exterior wall 161 of the vacuum chamber can 104 under an overwrap 162 of insulation and shrinkwrap. The flexible heating elements 160 are controlled by external heater power control 164 for coarse temperature adjustment. The internal heater power control 156 can be used for fine temperature adjustment.

A test controller 166 interfaces to one or more of the afore-mentioned active components to sense values, and to control a testing procedure than can be executed by one or more processors 168 as a test program 170 in memory 172. The test controller 166 can respond to user inputs via a user interface device 174 and can record test data 176 for later analysis and test reporting.

Figure 4:
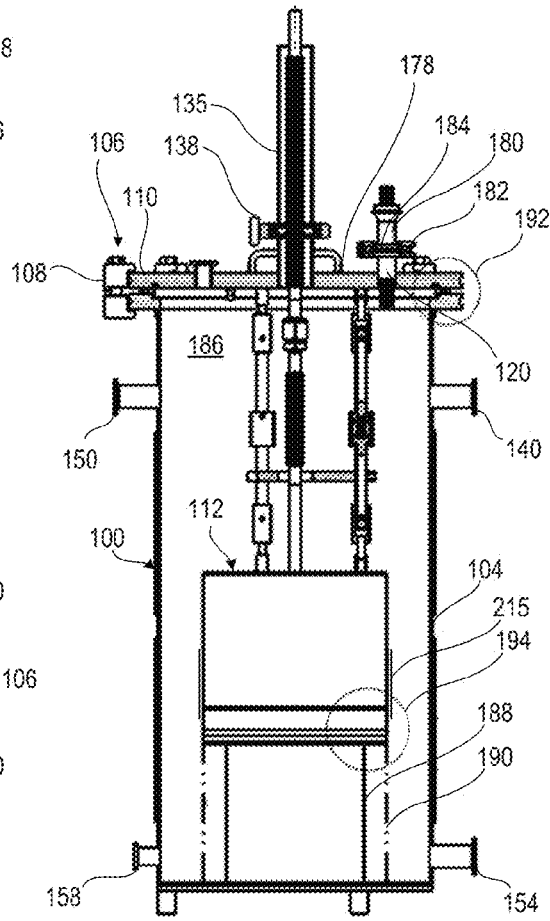
FIG. 4 illustrates a side view of the Cryostat-500 assembly of FIG. 3 in cross section along lines A-A, according to one embodiment.

A pair of handles 178 present upwardly from the vacuum chamber lid 110 can support the vacuum chamber lid assembly 106 including the cold mass vessel 112 during insertion into the vacuum chamber can 104. In FIGS. 3-4, port B 120 receives an electrical feedthrough 180, electrical feedthrough clamp 182, and centering ring with O-ring 184.

In FIG. 4, an interior space 186 of the Cryostat-500 assembly 100 is exposed to show that the vacuum chamber lid assembly 106 includes the cold mass vessel 112 that is supported from above by connection to the vacuum chamber lid 110. The cold mass vessel 112 is supported from below by a test specimen stand tube 188, which in an exemplary version is 6.00" dia.×0.250" thick wall formed of G-10 glass laminate tube and wrapped in aerogel blanket insulation 190 for 8" finished diameter. An upper cross-section portion 192 of the vacuum chamber lid assembly 106 is shown in greater detail in FIG. 5. A lower cross section portion 194 of the cold mass vessel 112 and test specimen stand tube 188 is shown in greater detail in FIG. 6.

Figure 5:
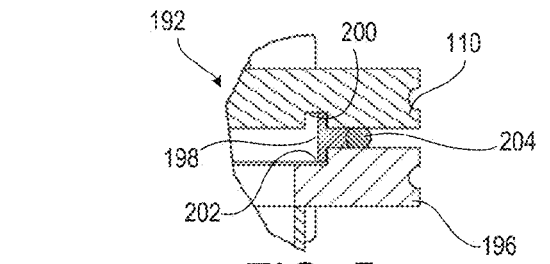
FIG. 5 illustrates a detail side view of an upper lip and vacuum chamber lid of the Cryostat-500 assembly of FIG. 4, according to one embodiment.

In FIG. 5, the vacuum chamber lid assembly 106 includes an upper lip 196 of the vacuum chamber can 104 that is clamped to the vacuum chamber lid 110. In between, a centering ring 198 is received in a downward annular groove 200 in an underside of the vacuum chamber lid 110 and an upward annular recess 202 in the upper lip 196 in order to position an O-ring 204.

Figure 6:
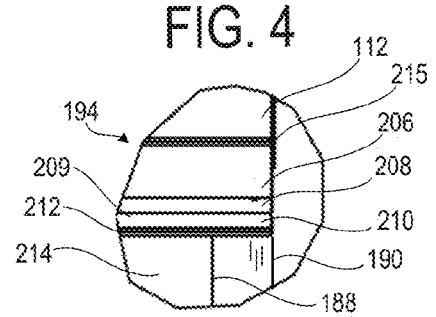
FIG. 6 illustrates a detail side view of a test specimen and underlying components of the Cryostat-500 assembly of FIG. 4, according to one embodiment.
Figure 6:
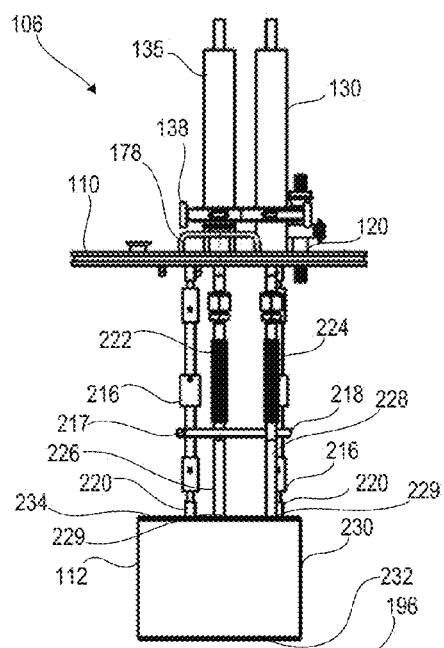
Figure 8:
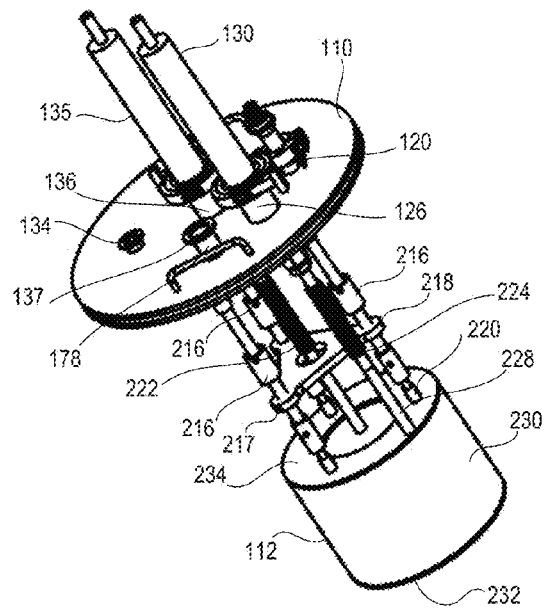
FIG. 8 illustrates an isometric view of the vacuum chamber lid assembly of FIG. 7, according to one embodiment.
Figure 7:
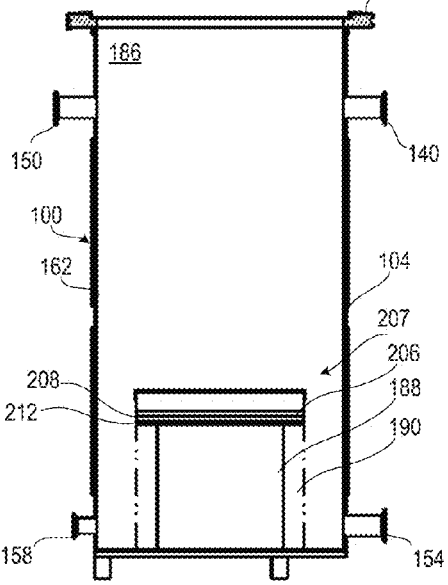
FIG. 7 illustrates a side view of a vacuum chamber lid assembly being lowered into the vacuum chamber can that is shown cutaway, according to one embodiment.
Figure 9:
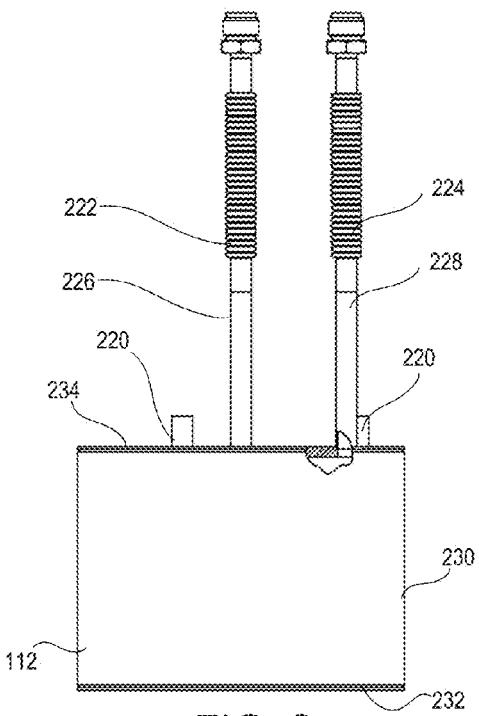
FIG. 9 illustrates a side view of a cold mass assembly of the vacuum chamber lid assembly of FIG. 8, according to one embodiment.
Figures 13, 14:
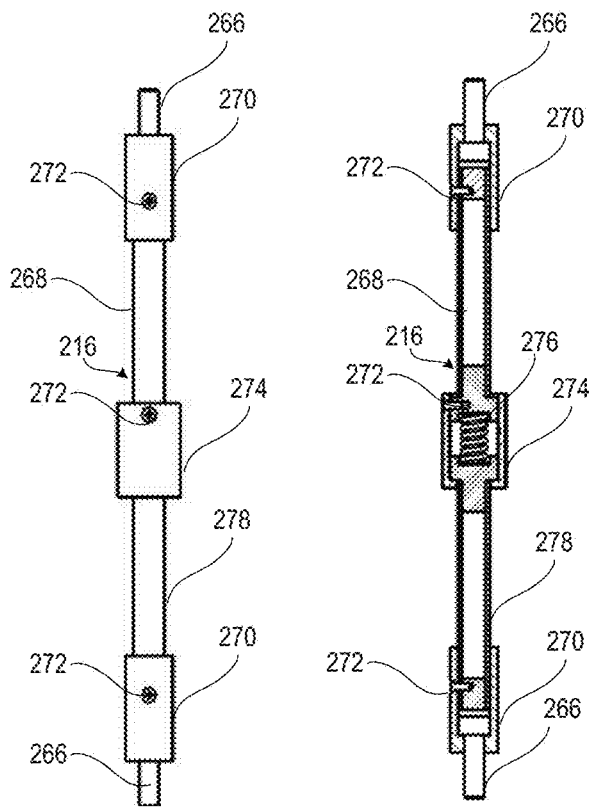
FIG. 13 illustrates a side view of a compliance rod assembly of the vacuum chamber lid assembly of FIG. 7, according to one embodiment.
FIG. 14 illustrates a side view in cross section of the compliance rod assembly of FIG. 13, according to one embodiment.

In FIG. 6, the cold mass vessel 112 sits atop a test specimen 206 (8.00" dia.×1.00" thickness), which in turn sits atop a warm boundary temperature surface. In an exemplary embodiment, the warm boundary temperature surface is formed from a heater plate assembly 207 of a conduction plate 208 (8.00" diameter×0.250" thickness copper), which in turn sits atop a flexible heater 209 and a heater plate 210 (8.00" diameter×0.250" thickness 6061-T6 aluminum plate), which in turn sits atop two compliance plates 212 (8.00" diameter×0.63" thickness pyrogel blanket) that rests on the top of the test specimen stand tube 188 that is filled with eight (8) Cryolite micro-fiberglass disks 214 (6.00" dia.×0.75" thickness). One or more temperature sensors may be imbedded within the upper conduction plate 208 to provide data output for control of the warm boundary temperature. The heater plate assembly may be integral to the test specimen stand tube 188 that is centered on the lower surface of the sealable chamber.

In FIGS. 4 and 6, a cold edge guard 215 wraps around a lower portion of the cold mass vessel 112 and an upper portion of the test specimen 206. For example, the cold edge guard 215 can be 3.00" wide and formed from 18 gauge copper sheet.

In FIGS. 7-10, the Cryostat-500 assembly 100 is depicted after the test specimen 206 is placed on the test specimen stand tube 188 and the cold mass vessel 112 is attached underneath the vacuum chamber lid 110 to form the vacuum chamber lid assembly 106. The cold mass vessel 112 is suspended by three radially spaced compliance rod assemblies 216 whose midpoints are stabilized by passing through, and held in place by set screws 217 (10-24UNC×0.375 SST) to, a compliance rod support guide 218 (6.00" diameter× 0.375" thickness Plexiglas acrylic sheet). The compliance rod assemblies 216 are attached at their lower end to respective threaded bosses 220 (0.500"×0.750" SST 304L bar) affixed to the cold mass vessel 112. The cold mass vessel 112 also includes a centered lower LN2 feedthrough 222 and an outer lower LN2 feedthrough 224 (SST 304L) that upwardly attach and communicate respectively with Port F 136 and Port C 126 and downwardly attach to tubes 226, 228 (0.500" OD×0.035" wall SST 304L tube) that extend from the cold mass vessel 112. The tubes 228 are sealed by respective ½" tube size Swagelok VCR connectors with copper or nickel gaskets and optional retainers 229. The outer portion of the cold mass vessel 112 includes a guard vessel wall 230 formed from a cylindrical sheet and closed by plates, specifically cold mass vessel bottom 232 and a guard vessel top 234, both of SST 304L (8.00" diameter×0.090" thickness).

In FIGS. 11-12, the cold mass vessel 112 encompasses a smaller cylindrically-shaped test vessel 236 having test vessel top 240 (SST 304L plate of 0.250" thickness), a test vessel outer wall 244 (SST 304L sheet of 0.090" thickness), and a test vessel inner wall 242 (SST 304L tube of 6.00" OD×0.250" wall machined to make 0.0900" thick inner wall), the latter two forming a lateral wall assembly 245. Lower ends of the test vessel inner and outer walls 242, 244 reside in an upwardly presented annular recess 246 in the cold mass vessel bottom 232. A thermal break is provided by a condensable vapor pocket 248 or void space between the test vessel inner and outer walls 242, 244 that is purged with $CO_2$ gas via a threaded boss 250 in a center of the cold mass vessel bottom 232. A ⅛ NPT plug 252 then closes the threaded boss 250 and the test vessel 236 is seal welded to retain the $CO_2$ gas. Other gases such as argon or other suitable material may be selected according to the testing temperature of the cold mass. In addition, high surface area, porous material may be retained within the condensable vapor pocket 248 to further inhibit heat transfer through the lateral wall assembly 245. Examples of porous material include silica aerogel, carbon black, fumed silica, or any other suitable material or combination of materials to further inhibit heat transfer through the lateral wall from the guard vessel to the test vessel by adsorption of the gas inside the thermal break. Attachment 254 between the test vessel inner and outer walls 242, 244 and the upwardly presented annular recess 246 are depicted in detail in FIG. 12.

With particular reference to FIG. 11, LN2 fills a guard cavity 256 within the cold mass vessel 112 via the tube 228. To fill a test cavity 258 within the test vessel 236, LN2 travels down through the centered lower LN2 feedthrough 222 and the tube 226 through an attached flexible tube 260 inside of the test vessel 236. The flexible tube 260 communicates through the test vessel top 240. The guard vessel top 234 and the test vessel top 240 have an upwardly presented circular recess 262, 264, respectively, to expedite vertical temperature stratification in the test cavity 258 and guard cavity 256 and provide maximum thermal stability within both cavities.

Figures 15, 16:
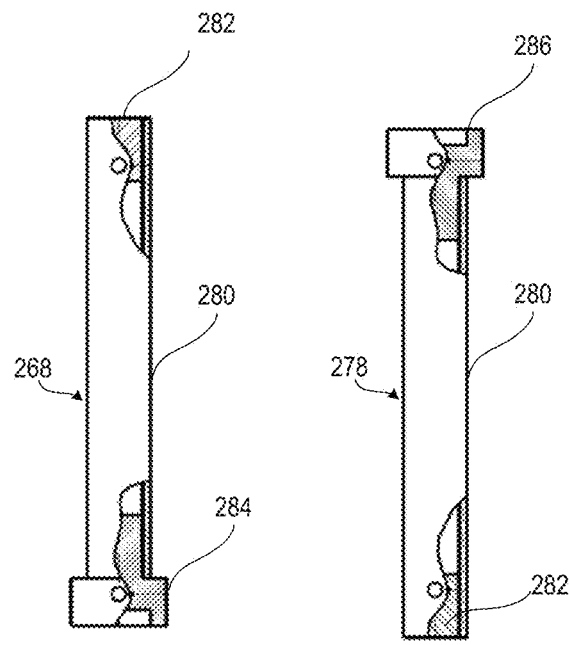
FIG. 15 illustrates a side view partially cutaway of a threaded pad tube assembly of the compliance rod assembly of FIG. 13, according to one embodiment.
FIG. 16 illustrates a side view partially cutaway of a non-threaded pad tube assembly of the compliance rod assembly of FIG. 13, according to one embodiment.

FIGS. 13-16 the compliance rod assembly 216 has a hex cap machine screw 266 (SST 5/16-18 gauge×1.00" long) received in a top and a threaded pad tube assembly 268 received in a bottom of an adjusting screw retainer 270 (6061-T6 aluminum bar of 0.75" dia.×1.675"), held by flat head machine screw 272 (SST #4-40×0.313). A bottom end of the threaded pad tube assembly 268 is received in a top of a compliance spring retainer 274 (6061-T6 aluminum bar of 1.00" diam.×1.50") above a compression spring 276 (SST 7/16 OD×11/16 fully relaxed (FR) long). Below the compression spring 276 is a similar but inverted assembly of a nonthreaded pad tube assembly 278, adjusting screw retainer 270 and hex cap machine screw 266. With particular reference to FIG. 15, the threaded pad tube assembly 268 includes a compliance rod tube 280 (G-10 glass fiber reinforced plastic laminate tube of 0.500"×3.650"×0.63" wall) that receives in its top a tube end plug 282 (Lexan or Plexiglas acrylic rod of 0.375" dia.×0.750") and receives in its bottom a threaded spring pad 284 (G-10 glass fiber reinforced plastic laminate rod of 0.75" dia.×0.875"). With particular reference to FIG. 16, the nonthreaded pad tube assembly 278 includes a compliance rod tube 280 (G-10 glass fiber reinforced plastic laminate tube of 0.500"× 3.650"×0.63" wall) that receives in its bottom a tube end plug 282 (Lexan or Plexiglas acrylic rod of 0.375" dia.× 0.750") and receives in its top a non-threaded spring pad 286 (G-10 glass fiber reinforced plastic laminate rod of 0.75" dia.×0.875").

Thus, a suspension system for the cold mass assembly is low thermal conductivity and is comprised of adjustable compliance rod assemblies 216 for a given test specimen thickness and for amount of compression force. Upper and lower halves rotate independently to provide length-wise adjustment with the test apparatus fully assembled and with or without mechanical loads. In particular, the suspension system for the cold mass assembly includes a connector assembly with a mechanical compliance element consisting of a spring or spacer rod to enable testing of fully rigid or fully flexible test specimens.

The present invention provides information for the laboratory measurement of the steady-state thermal transmission properties and heat flux of thermal insulation systems undergoing cryogenic operating conditions. Thermal insulation systems may be comprised of one or more specimens that may be homogenous or non-homogenous at boundary conditions from 4 K to 400 K and in environments from high vacuum to ambient pressure of residual gas. The testing methods employed with the present invention are distinct from, and yet complementary to, other ASTM thermal test methods.

The function of most cryogenic thermal insulation systems used in these applications is to maintain large temperature differentials (delta-T) thereby providing high levels of thermal insulation performance. Cold boundary temperatures range from 4 K to 100 K or higher. Warm boundary temperatures (WBT) range from 250 K up to 400 K (77 K to 100 K WBT for some cases). Temperature differentials of up to 300 K are typically present. The large temperature differentials, in the low temperature range, are impractical to execute and obtain accurate results using other ASTM International test methods such as C177 and C518.

The range of residual gas pressures is from $10^{-7}$ to $10^{+3}$ torr ($1.33^{-5}$ Pa to 133 kPa) with different purge gases as required. Corresponding to the application in cryogenic systems, three sub-ranges of vacuum are also defined: High Vacuum (HV) from <$10^{-6}$ torr to $10^{-3}$ torr ($1.333^{-4}$ Pa to 0.133 Pa) [free molecular regime], Soft Vacuum (SV) from $10^{-2}$ torr to 10 torr (from 1.33 Pa to 1.333 Pa) [transition regime], No Vacuum (NV) from 100 torr to 1000 torr (13.3 kPa to 133 kPa) [continuum regime]. Over the full vacuum pressure range, thermal performance can vary nearly four orders of magnitude. The range of effective thermal conductivity is from 0.010 to 100 mW/m-K, with concentrations in the range of 0.05 to 2 mW/m-K for high vacuum insulation systems and 10 to 25 mW/m-k for no vacuum systems.

Soft vacuum systems are generally in between the discussed extremes. Of particular interest and demand is the low to very low thermal conductivity (high thermal resistance) range where other ASTM test methods are impractical for obtaining any meaningful results.

Careful delineation of test results in the range of 0.01 to 1 mW/m-K is required as a matter of normal engineering applications for many cryogenic insulation systems. The Cryostat-500 assembly comprising the present invention includes the handling tools, instrumentation, methodology, data acquisition, data reporting, filling funnels, and ancillary equipment needed to provide consistent scientific and engineering results in a cost-effective, safe, reliable, and practical manner.

An understanding of some of the novel features of the Cryostat-500 assembly will become readily apparent from the following discussion. A key aspect in understanding thermal performance of cryogenic insulation systems is performing tests under representative conditions, simulating the way the materials are actually put together and used in service. Therefore, a large temperature differential across the insulation and a residual gas environment at some specific pressure are usually required. Added to these requirements are the complexities of thickness measurement at test conditions after thermal contraction, verification of surface contact and/or mechanical loading after cool down, and measurement of high vacuum levels within the material. The thermal performance levels are often very high: for example, heat flux (q) values below 0.5 mW/m² and effective thermal conductivity ($k_e$) below 0.05 mW/m-K are not unusual.

At these very low heat leakage rates, on the order of tens of milliwatts on the average size apparatus, all details in approach, design, installation, and execution must be carefully considered and worked out to obtain a meaningful result. For example, lead wires for temperature sensors must be smaller diameter, lengthy, and carefully installed. In the case of boiloff testing, atmospheric pressure effects, starting condition of the cryogen, and vibration forces from surrounding facilities are just a few of the problems that are successfully resolved by the Cryostat-500 assembly.

The Cryostat-500 assembly, consistent with aspects of the present invention, can be extended to other (higher) temperatures as well, even up to 373 K in the case of using water as the heat measurement fluid. Boiloff testing may be performed with a number of cryogens or refrigerants with normal boiling points below ambient temperature. The cold boundary temperature is usually fixed but can be easily adjusted higher by interposing a thermal resistance layer (such as a polymer, composite, or other suitable material) between the cold mass and the specimen being tested. However, thermal contact resistance must be fairly well understood and obtaining a specific cold-side temperature can require precise actions.

Liquid nitrogen (77 K) is the most commonly used cryogen due to its low cost, relative ease of handling, a cold boundary temperature generally representative of many applications, and the minimal vapor correction that is required (compared to hydrogen or helium). Liquid hydrogen (20 K) can be used with the proper additional safety precautions for working with a flammable fluid. Liquid helium (4 K) can also be used effectively, but with a significant rise in expense and complexity. The thermal performance, or heat flow rate (J/s), is a direct relation to the boiloff mass flow rate (g/s) by the heat of vaporization (J/g) of the liquid. Boiloff methods are, therefore, direct with respect to calculating an effective thermal conductivity or heat flux.

Figure 17:
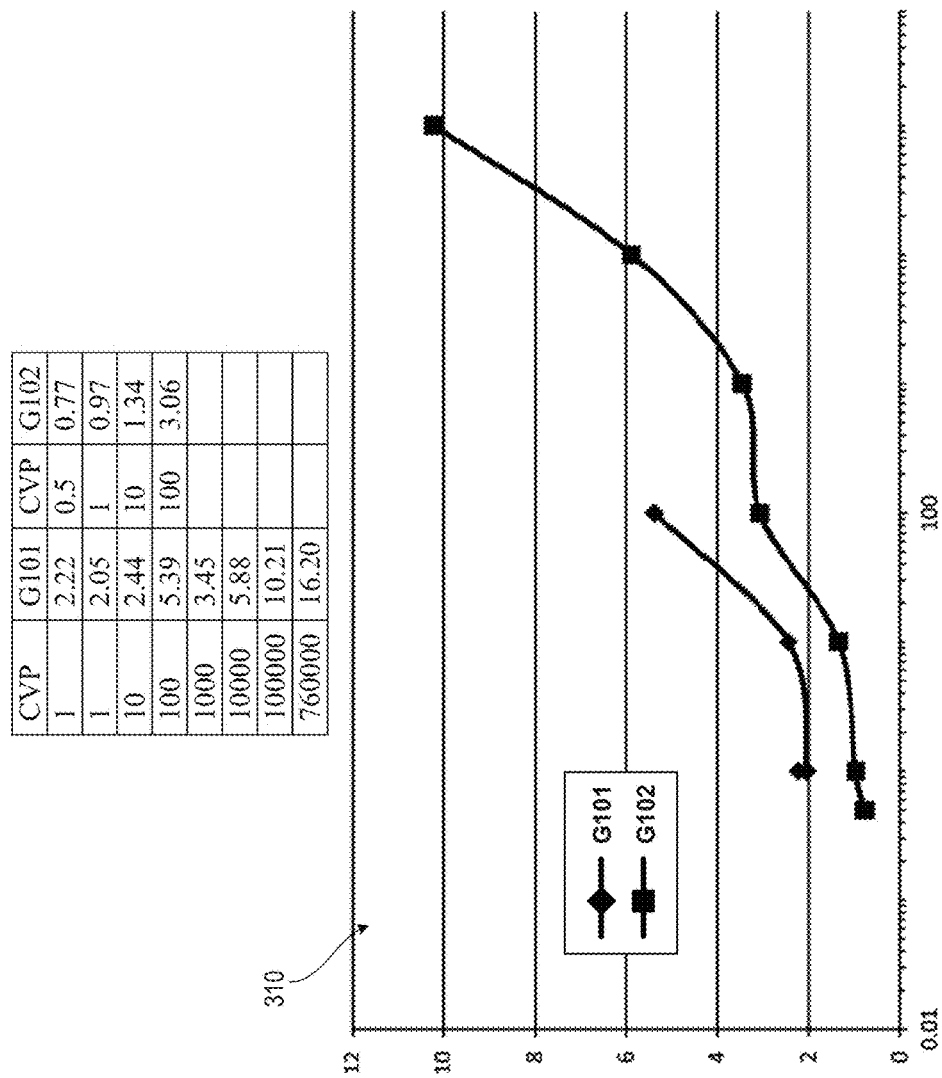
FIG. 17 illustrates a graphical plot of the variation of effective thermal conductivity ($k_e$) (mW/m-K) with cold vacuum pressure (CVP) (millitorr)

FIG. 17 illustrates a graphical plot 310 of the variation of effective thermal conductivity ($k_e$) (mW/m-K) with cold vacuum pressure (CVP) (millitorr).

Experimental Test Results for C-500 Assembly

Cryostat-500 Assembly Thermal Performance Testing of Four Thick Aerogel/MLI Composite Test Articles: Cryostat thermal performance testing of four thick Aerogel/MLI composite test articles was performed by the Cryogenics Test Laboratory at the NASA Kennedy Space Center.

The physical characteristics of four 200-mm diameter disk type test articles are summarized in Table 1. The test articles were received in clean room packaging and the cold sides were designated for test installation. Each test article consisted of a total of four layers of lightweight aerogel thin blanket (aerogel blanket) and a large number of layer pairs of double aluminized Mylar with polyester netting (MLI) assembled in one of four different combinations. Each test article was enclosed within 1-mil aluminized Mylar face sheets and supported by six evenly spaced edge spacers.

TABLE 1

Summary of Physical Characteristics of Test Articles

| Test Series | Description | Thickness* mm | Weight g | Diameter mm | Density* kg/m³ |
|---|---|---|---|---|---|
| G132 | Prototype #1 - two aerogels on each side, MLI in middle | 22.9 | 41.4 | 197 | 59.3 |
| G133 | Prototype #2 - MLI on warm side, aerogel pair, MLI, divided aerogel pair | 23.2 | 50.4 | 207 | 64.4 |
| G136 | Prototype #3 - MLI, four aerogels in middle, MLI | 20.2 | 47.6 | 210 | 67.6 |
| G137 | Prototype #4 - MLI on warm side, four aerogels on cold side | 25.3 | 51.3 | 208 | 59.8 |

*As tested.

The testing was performed using Cryostat-500 assembly, a flat-plate guarded liquid nitrogen boiloff calorimeter. The Cryostat-500 assembly with its 203-mm diameter thermally-guarded cold mass was used in accordance with laboratory standard methods. The instrument and method of heat measurement are absolute in that the cold mass test vessel is fully thermally guarded by a guard vessel. The instrument does, however, include a calibration feature made possible by an adjustable edge guard ring that is positioned about the circumference of the test specimen. In this case, all tests were performed with a copper edge guard ring at the 50% thickness position.

Figure 18:
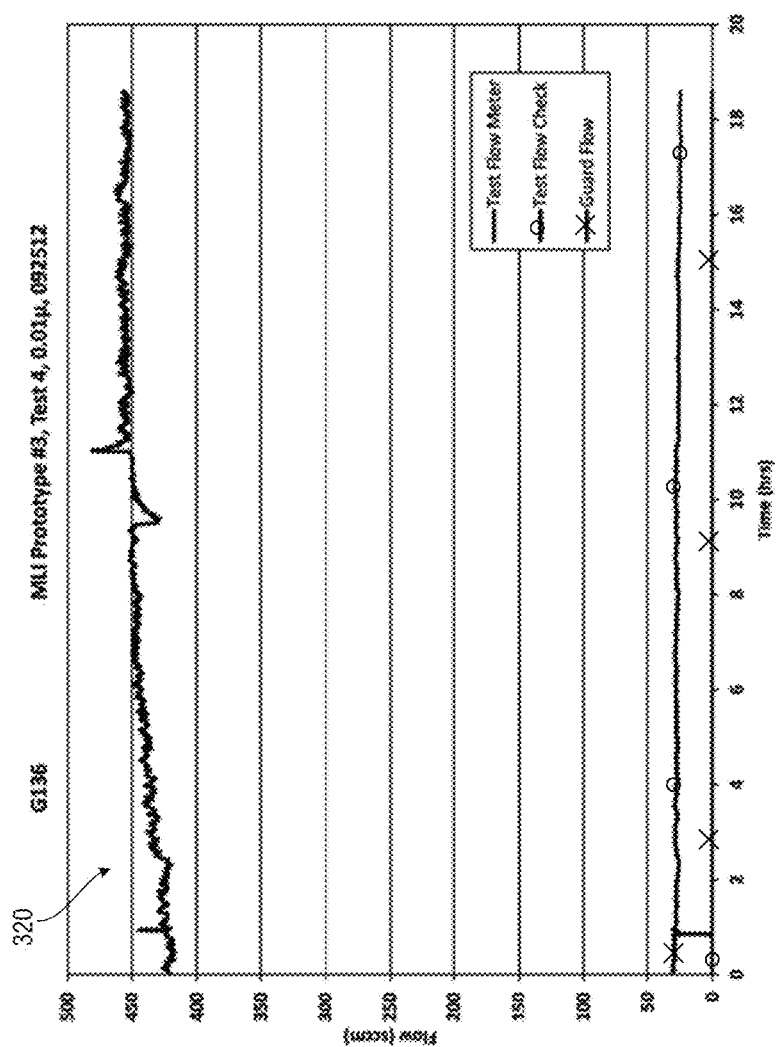
FIG. 18 illustrates a graphical plot of an example of the nitrogen boiloff flow rate for G136, Test 4, at the high vacuum condition.
Figure 19:
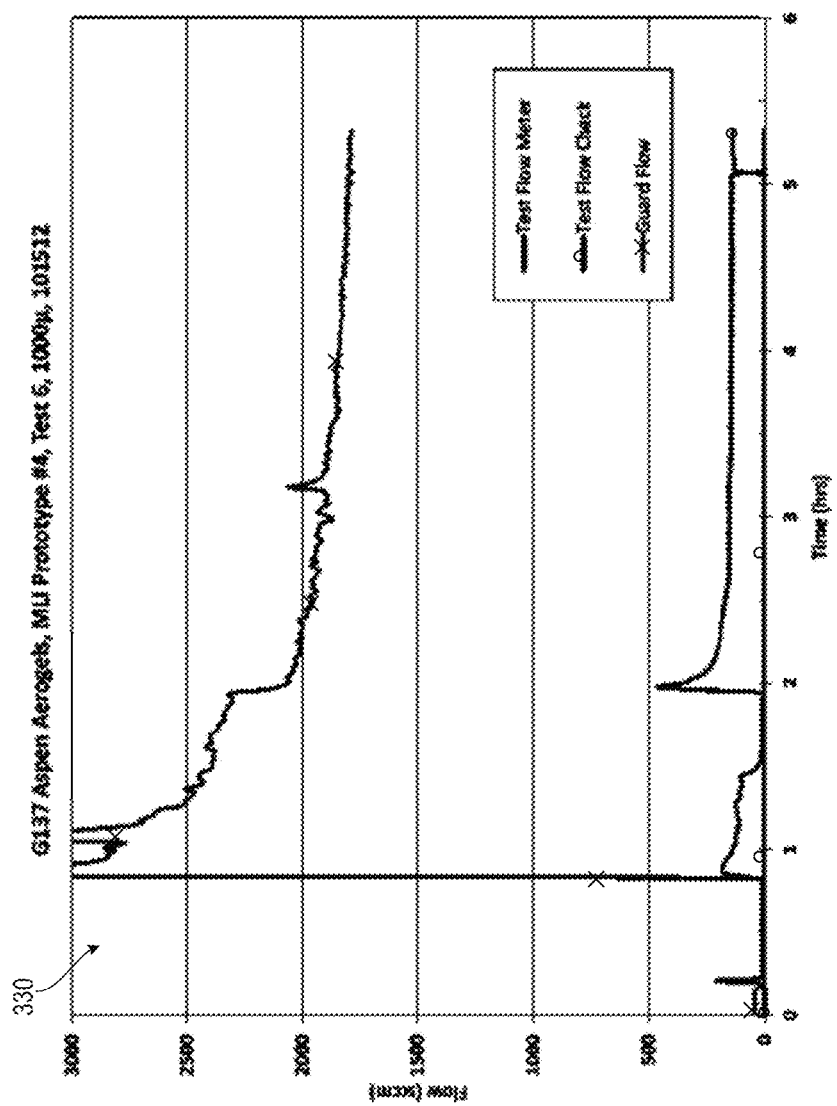
FIG. 19 illustrates a graphical plot of an example of the nitrogen boiloff flow rate for G137, Test 6, at the soft vacuum (1000 millitorr) condition.
Figure 20:
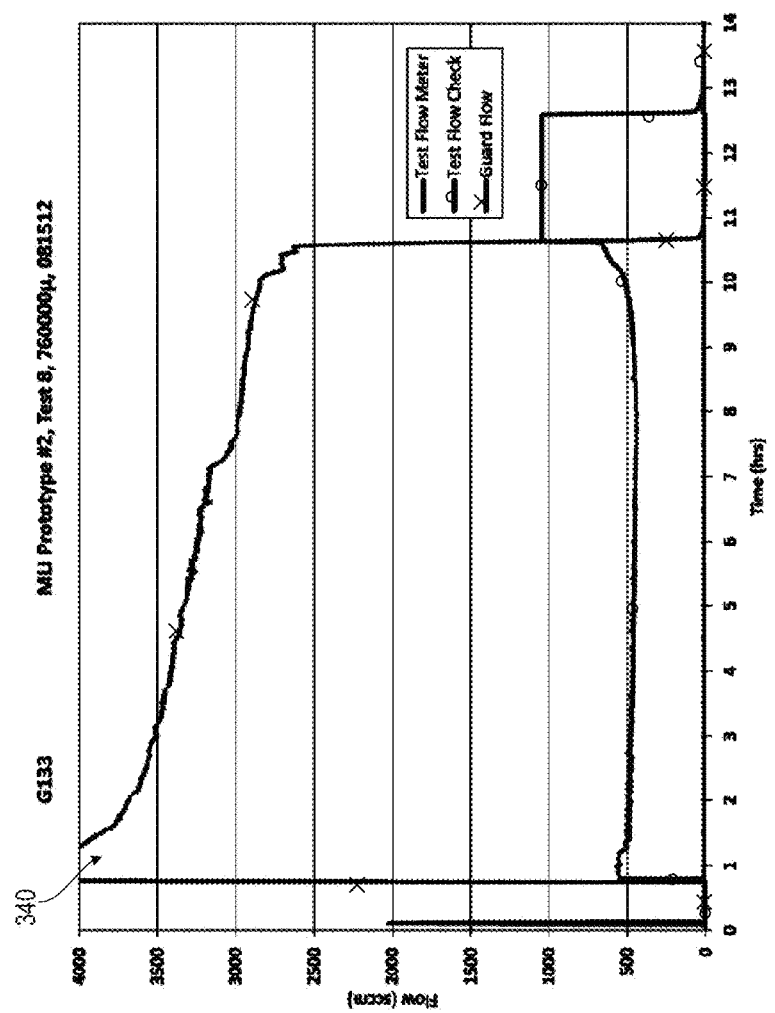
FIG. 20 illustrates a graphical plot of an example of the nitrogen boiloff flow rate for G133, Test 8, at the no vacuum condition.

The results are calculated in both heat flux (q) [W/m$^2$] and effective thermal conductivity ($k_e$) [mW/m-K]. The boundary temperatures were approximately 78 K and 293 K for all tests. The CVP ranged from high vacuum (below 1×10$^{-5}$ torr), to soft vacuum, and up to 760 torr (ambient pressure). The residual gas was nitrogen for all tests other than high vacuum. Example plots of the nitrogen boiloff flow rates (for both the test vessel and the guard vessel) are given in FIGS. 18-20. FIG. 18 illustrates a graphical plot 320 of an example of the nitrogen boiloff flow rate for G136, Test 4, at the high vacuum condition. FIG. 19 illustrates a graphical plot 330 of an example of the nitrogen boiloff flow rate for G137, Test 6, at the soft vacuum (1000 millitorr) condition. FIG. 20 illustrates a graphical plot 340 of an example of the nitrogen boiloff flow rate for G133, Test 8, at the no vacuum condition.

Figure 21:
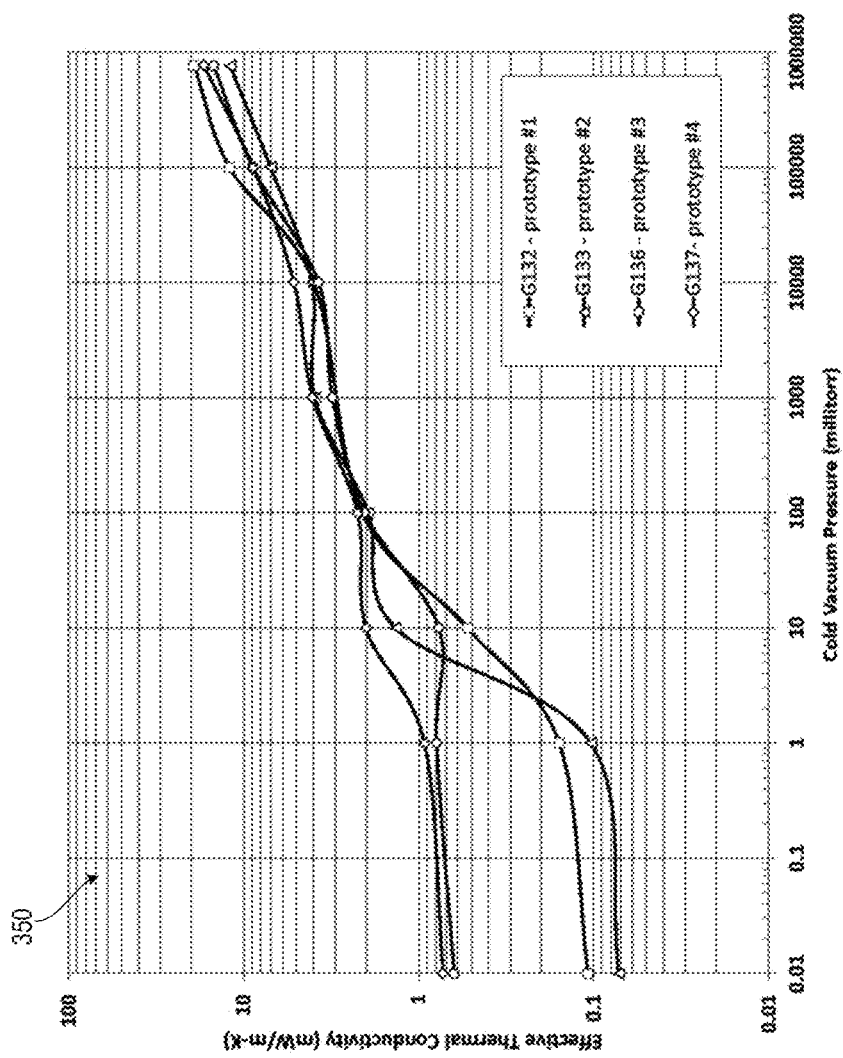
FIG. 21 illustrates a graphical plot of the variation of effective thermal conductivity ($k_e$) with CVP for several layered composite insulation systems at the boundary temperatures of 293 K and 78 K and a residual gas of nitrogen.
Figure 22:
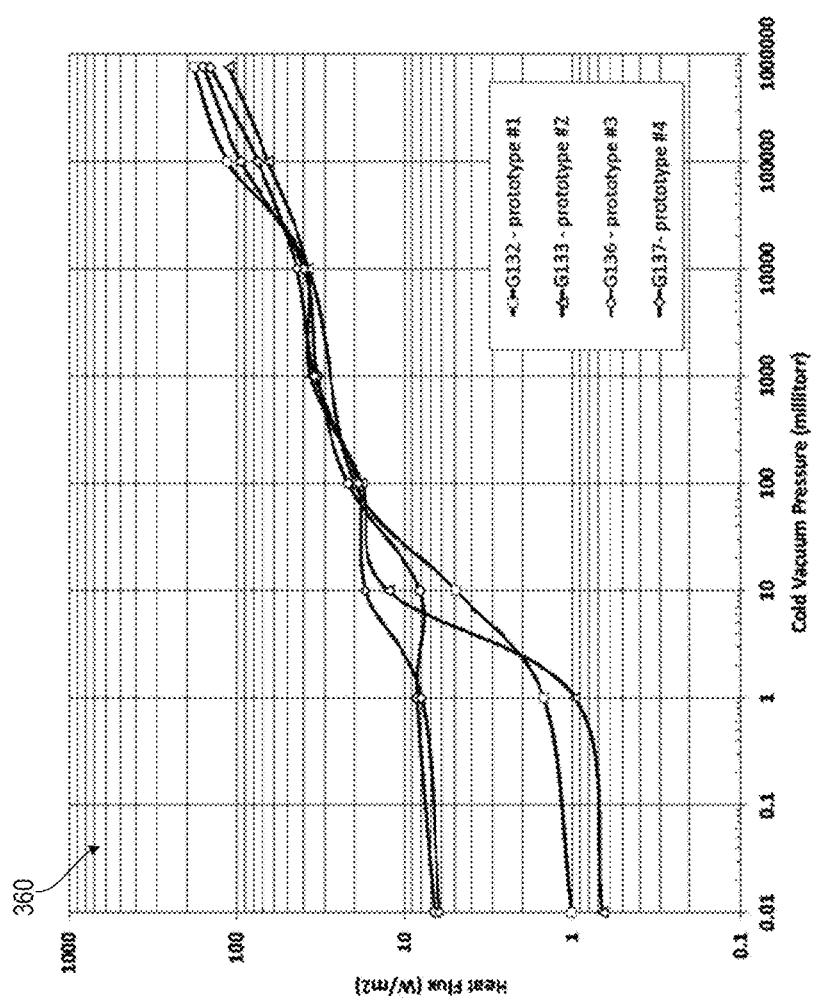
FIG. 22 illustrates a graphical plot of the variation of heat flux (q) (W/m$^2$) with cold vacuum pressure.

A summary of all Cryostat-500 assembly test results for test series G132, G133, G136, and G137 is given in TABLE 2 for variation of effective thermal conductivity ($k_e$) with cold vacuum pressure (CVP). Boundary temperatures were approximately 293 K and 78 K. The residual gas was nitrogen. FIG. 21 illustrates a graphical plot 350 of the variation of $k_e$ with CVP. FIG. 22 illustrates a graphical plot 360 of the variation of heat flux (q) with CVP. Boundary temperatures are approximately 293 K and 78 K; the residual gas is nitrogen.

TABLE 2

Summary of Test Results for Cryostat-500 assembly
Test Series G132, G133, G136, and G137

| Test Series | Description | CVP** millitorr | Boiloff Flow Rate sccm | $k_e$* mW/m-K | Heat Flux (q)* W/m$^2$ |
|---|---|---|---|---|---|
| G132 | Prototype #1 | <0.01 | 4.1 | 0.108 | 1.01 |
|  |  | 1 | 6.0 | 0.158 | 1.48 |
|  |  | 10 | 20 | 0.526 | 4.94 |
|  |  | 100 | 80 | 2.11 | 19.8 |
|  |  | 1000 | — | — | — |
|  |  | 10000 | 152 | 4.00 | 37.6 |
|  |  | 100000 | 460 | 12.1 | 114 |
|  |  | 760000 | 731 | 19.2 | 181 |
| G133 | Prototype #2 | <0.01 | 2.7 | 0.072 | 0.667 |
|  |  | 1 | 3.9 | 0.104 | 0.963 |
|  |  | 10 | 51 | 1.36 | 12.6 |
|  |  | 100 | 73 | 1.95 | 18.0 |
|  |  | 1000 | 147 | 3.92 | 36.3 |
|  |  | 10000 | 153 | 4.08 | 37.8 |
|  |  | 100000 | 264 | 7.04 | 65.2 |
|  |  | 760000 | 450 | 12.0 | 111 |
| G136 | Prototype #3 | <0.01 | 27 | 0.628 | 6.67 |
|  |  | 1 | 34 | 0.791 | 8.40 |
|  |  | 10 | 33 | 0.769 | 8.15 |
|  |  | 100 | 88 | 2.05 | 21.7 |
|  |  | 1000 | 134 | 3.12 | 33.1 |
|  |  | 10000 | 161 | 3.75 | 39.8 |
|  |  | 100000 | 383 | 8.91 | 94.6 |
|  |  | 760000 | 638 | 14.8 | 158 |
| G137 | Prototype #4 | <0.01 | 25 | 0.725 | 6.18 |
|  |  | 1 | 32 | 0.929 | 7.90 |
|  |  | 10 | 69 | 2.01 | 17.04 |
|  |  | 100 | 77 | 2.24 | 19.02 |
|  |  | 1000 | 139 | 4.04 | 34.3 |
|  |  | 10000 | 178 | 5.17 | 44.0 |
|  |  | 100000 | 305 | 8.86 | 75.3 |
|  |  | 760000 | 582 | 16.9 | 144 |

*Boundary temperatures are approximately 293 K. and 78 K.
**CVP = Cold Vacuum Pressure (residual gas is nitrogen)

Cryostat-500 assembly Thermal Performance Testing of Two Aerogel/MLI Composite Test Articles: Cryostat thermal performance testing of two Aerogel/MLI composite test articles was performed by the Cryogenics Test Laboratory at the NASA Kennedy Space Center. The design configuration of the two similar test articles is given as follows: three layers of aerogel blanket with one layer of ¼-mil double-aluminized mylar (DAM) between each aerogel layer; top and bottom include 1-mil DAM; fit with six edge stiffeners, evenly spaced. The physical characteristics of the pair of 203-mm diameter disk type specimens are summarized in TABLE 3.

TABLE 3

Summary of Physical Characteristics of Test Articles

| Test Series | Description | Thickness* mm | Weight g | Diameter mm |
|---|---|---|---|---|
| G134 | Prototype #1, 3 layers aerogel, ¼-mil DAM, 1-mil DAM top & bottom, six evenly spaced 25-mm legs | 10.7 | 15.0 | 203 |
| G135 | Prototype #2 (same design) | 8.8 | 14.6 | 203 |

*As tested

The testing was performed using Cryostat-500 assembly, a flat-plate guarded liquid nitrogen boiloff calorimeter. The Cryostat-500 assembly with its 203-mm diameter thermally-guarded cold mass was used in accordance with laboratory standard methods. The instrument and method of heat measurement are absolute in that the cold mass test vessel is fully thermally guarded by a guard vessel. The instrument does, however, include a calibration feature made possible by an adjustable edge guard ring that is positioned about the circumference of the test specimen. In this case, all tests were performed with a copper edge guard ring at the 50% thickness position.

Figure 23:
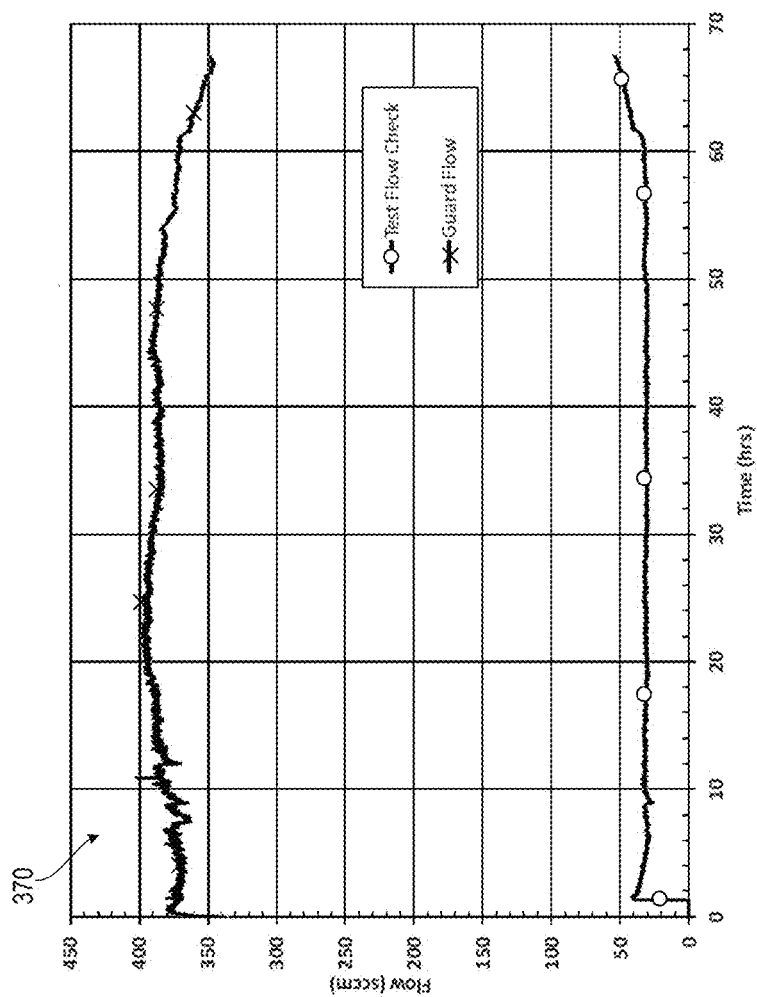
FIG. 23 illustrates a graphical plot of an example of the nitrogen boiloff flow rate for G134, Test 4, at the high vacuum condition.
Figure 24:
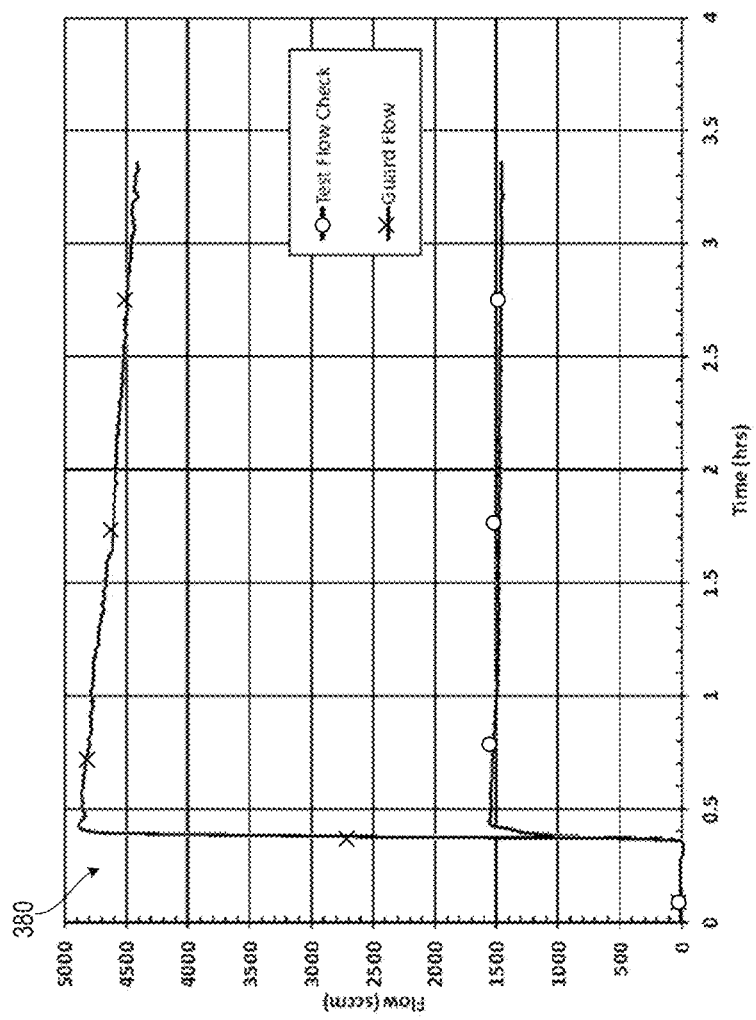
FIG. 24 illustrates a graphical plot of an example of the nitrogen boiloff flow rate for G135, Test 8, at the no vacuum condition.

The results are calculated in both heat flux (W/m$^2$) and effective thermal conductivity or k$_e$ (mW/m-K). The boundary temperatures were approximately 78 K and 293 K for all tests. The cold vacuum pressures ranged from high vacuum (below 1×10-5 torr), to soft vacuum, and up to 760 torr (ambient pressure). The residual gas was nitrogen for all tests other than high vacuum. Example plots of the nitrogen boiloff flow rates (for both the test vessel and the guard vessel) are given in FIGS. 23-24. FIG. 23 illustrates a graphical plot 370 of an example of the nitrogen boiloff flow rate for G134, Test 4, at the high vacuum condition. FIG. 24 illustrates a graphical plot 380 of an example of the nitrogen boiloff flow rate for G135, Test 8, at the no vacuum condition.

A summary of all Cryostat-500 assembly test results for test series G134 and G135 is given in TABLE 4.

TABLE 4

Summary of Test Resultsfor Cryostat-500 assembly Test Series G134 and G135.

| Test Series | Description | CVP** millitorr | Boiloff Flow Rate sccm | k$_e$* mW/ m-K | Heat Flux (q)* W/m$^2$ |
|---|---|---|---|---|---|
| G134 | Prototype #1 | <0.01 | 32 | 0.393 | 7.9 |
|  |  | 1 | 58 | 0.711 | 14.3 |
|  |  | 10 | 123 | 1.51 | 30.4 |
|  |  | 100 | 146 | 1.80 | 36.1 |
|  |  | 1000 | 200 | 2.46 | 49.4 |
|  |  | 10000 | 249 | 3.06 | 61.5 |
|  |  | 100000 | 517 | 6.34 | 128 |
|  |  | 760000 | 1270 | 15.58 | 314 |
| G135 | Prototype #2 | <0.01 | 21 | 0.212 | 5.2 |
|  |  | 1 | 38 | 0.385 | 9.4 |
|  |  | 10 | 70 | 0.709 | 17.3 |
|  |  | 100 | 168 | 1.70 | 41.5 |
|  |  | 1000 | 289 | 2.92 | 71.4 |
|  |  | 10000 | 500 | 5.06 | 124 |
|  |  | 100000 | 1125 | 11.36 | 278 |
|  |  | 760000 | 1476 | 14.92 | 365 |

*Boundary conditions are approximately 293 K. and 78 K.
**CVP = Cold Vacuum Pressure (residual gas is nitrogen)

Figure 25:
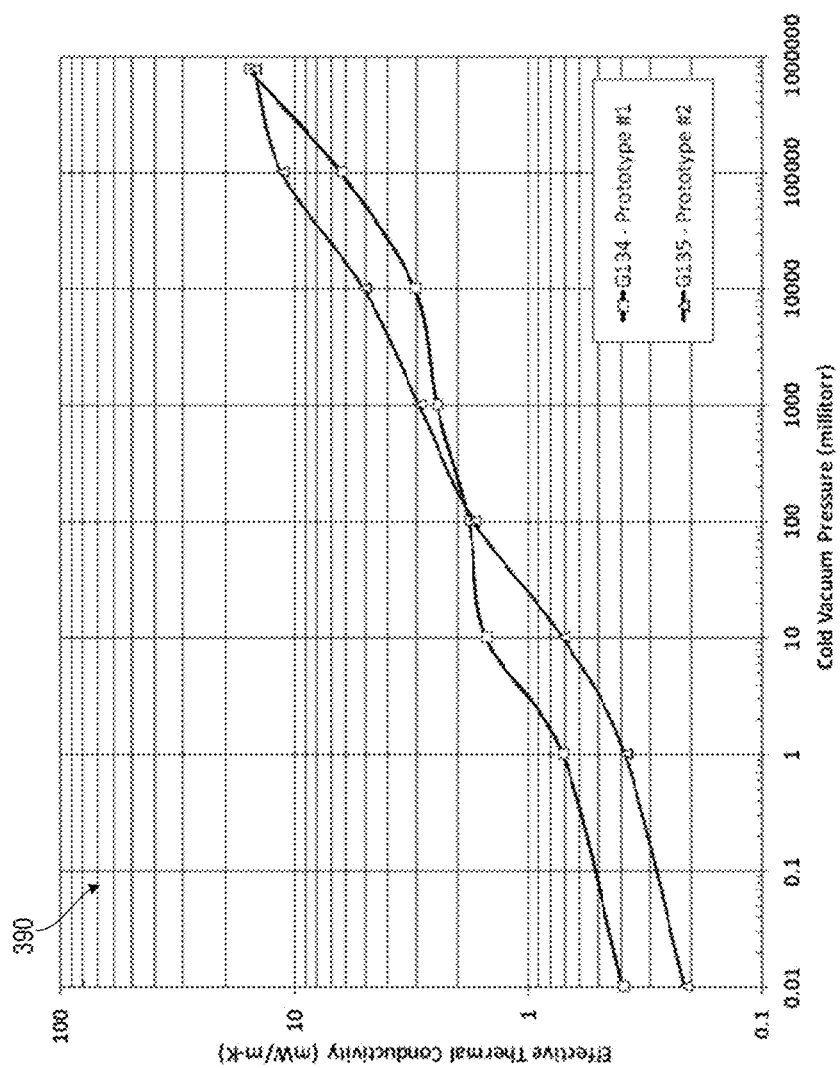
FIG. 25 illustrates a graphical plot of variation of effective thermal conductivity with cold vacuum pressure for Cryostat-500 assembly test series G134 and G135.
Figure 26:
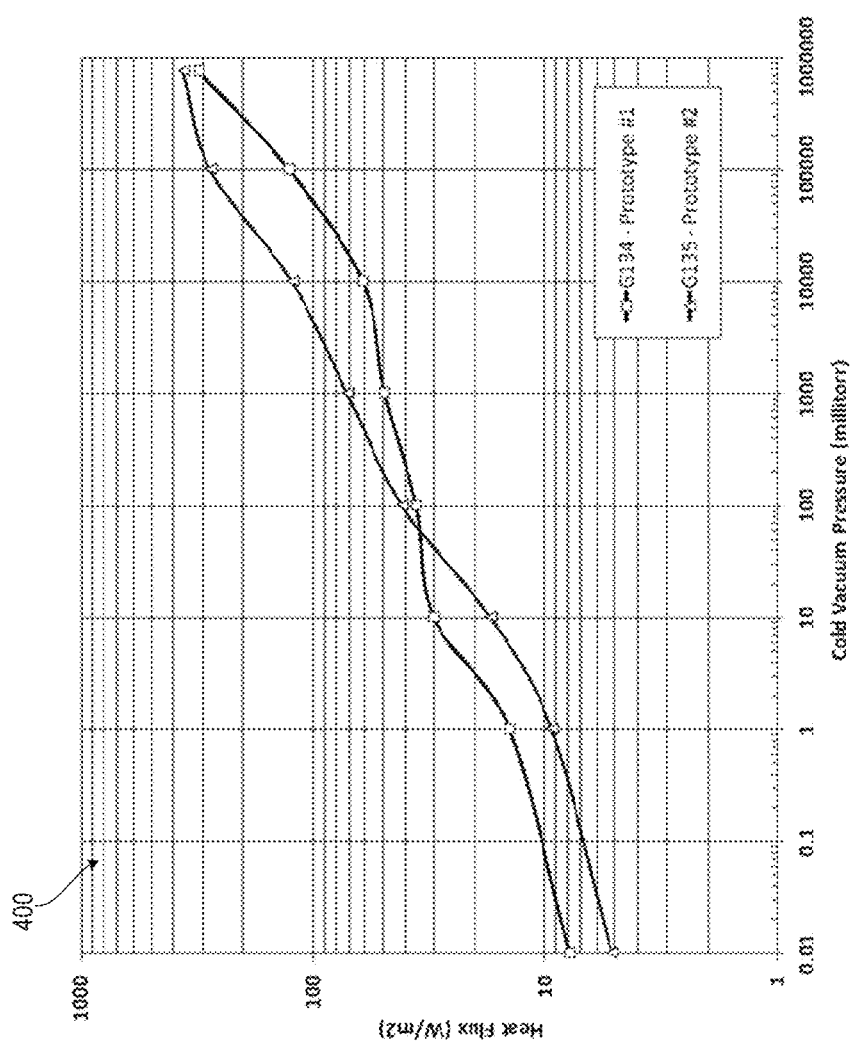
FIG. 26 illustrates a graphical plot of variation of heat flux with cold vacuum pressure for Cryostat-500 assembly test series G134 and G135.

FIG. 25 illustrates a graphical plot 390 of variation of effective thermal conductivity (k$_e$) with cold vacuum pressure for Cryostat-500 assembly test series G134 and G135. Boundary temperatures are approximately 293 K and 78 K; the residual gas is nitrogen. FIG. 26 illustrates a graphical plot 400 of variation of heat flux with cold vacuum pressure for Cryostat-500 assembly test series G134 and G135. Boundary temperatures are approximately 293 K and 78 K; the residual gas is nitrogen.

LABORATORY STANDARD TEST PROCEDURE: CTL-TP-038, Flat Plate Insulation Test: The Guarded Flat Plate Insulation Test Cryostat (Cryostat-500 assembly) is a boiloff calorimeter comprised of a flat bottom test apparatus for measuring the absolute thermal performance of an insulation test article. Typical dimensions allow accepting test specimens 200 mm in diameter by up to 30 mm thick. Temperature sensors are located on the side of the apparatus in addition to the boundary temperatures. The test vessel or chamber is guarded by a cryogen or guard chamber. System insulation materials provide additional thermal stability for testing over a wide range of environmental conditions. The cold-mass assembly can be configured for rigid or soft materials, with or without compressive loads.

Figure 27:
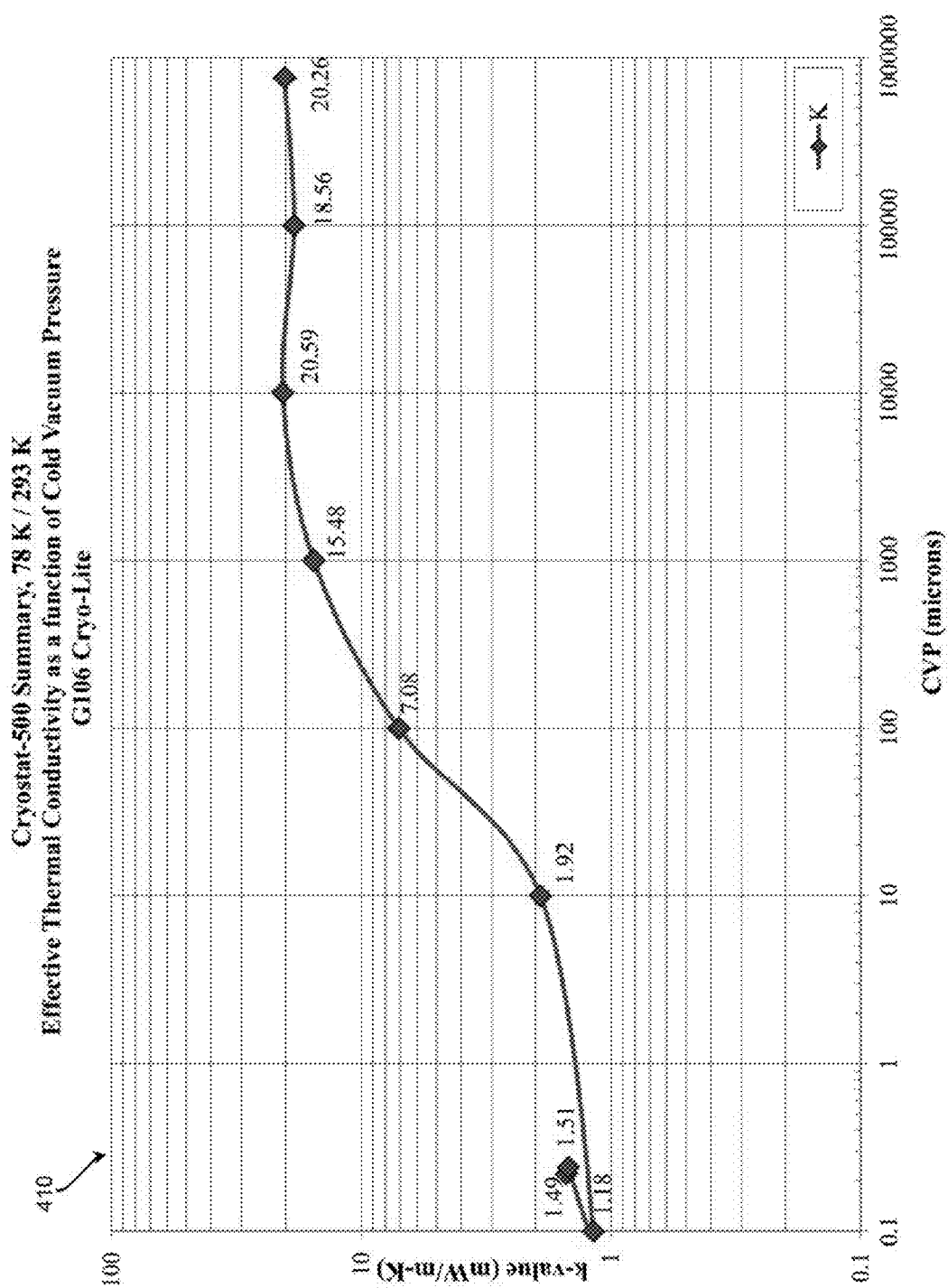
FIG. 27 illustrates a graphical plot of example results of 78 K/293 K for effective thermal conductivity as a function of cold vacuum pressure for G106 Cryo-Lite.

FIG. 27 illustrates a graphical plot 410 of example results of 78 K/293 K for effective thermal conductivity as a function of cold vacuum pressure for G106 micro-fiberglass material (Cryo-Lite).

The Cryostat-500 assembly follows from the technology of Cryostat-100 assembly (cylindrical, absolute boiloff calorimeter) and Cryostat-400 (flat plate, comparative boiloff calorimeter). The new system allows for the testing of a convenient size and shape of insulation materials and provides a direct route for obtaining absolute thermal conductivity and heat flux data. The Cryostat-100 assembly provides absolute data but requires a fairly large cylindrical specimen that may not be available or may not be representative of the desired insulation system application. The Cryostat-400 instrument allows a convenient specimen size of around 200-mm diameter, but provides comparative data that must be further referenced or calibrated against a standard reference material. (Worldwide, these standard reference materials are still in the formative stages for the cryogenic cases.) There is a basic need for thermal performance data on insulation materials and systems that operate at below ambient temperatures. This need is being driven by more demand for cryogenic applications in electrical power, energy storage, ground and air transportation, medical imaging, food processing, electronics manufacturing, and space launch and exploration. The performance requirements are also increasing due to steadily increasing demands through energy-efficiency standards in building construction, refrigeration systems, and all energy-related sectors of business and commerce. The previously described technology available today (Cryostat-100 assembly and Cryostat-400 assembly, etc.) are complementary but inadequate to meet the new demands. The new technology is also complementary, in part, to the existing commercial instruments (i.e., ASTM C177 Guarded Hot Plate) but goes far beyond the existing standards in regard to both precision for very-low thermal conductivity conditions as well as the practicality of testing under the representative conditions of cryogenic and vacuum. Finally, the Cryostat-500 assembly provides a cost-effective way to obtain precision data on high-performance materials under actual-use conditions. To this end, a new testing standard, ASTM C1774, *Standard Guide to Thermal Performance Testing of Cryogenic Insulation Systems*, was developed under ASTM International.

The Cryostat-500 assembly provides a much wider range of heat flux performance and over the full range of environmental conditions including vacuum levels from 10$^{-7}$ to 10$^{+3}$ torr. The instrument has been proven through extensive testing of multilayer insulation (MLI) systems, aerogel blankets, fiberglass, foams, etc. Both the quality and quantity of the thermal performance data for insulation materials and systems have increased even as the process and method has become more time efficient and cost effective.

The specialized methods, tools, and equipment of the present invention have been successfully developed and proven for safe operation and reliable results. The combination of cold mass design, vacuum chamber design, and ancillary equipment, along with these methods, make the high testing rate and high data quality a nearly hands-off operation. Installation is simplified and operation is accomplished by periodic tending of the instrument over several hours or several days, as the case may be. The core of the technology is the cold mass design which is based on a stratified liquid approach and includes stepped liquid levels and features a vapor pocket interior wall. These crucial elements ensure that the heat energy being measured by the test chamber is passing only through the desired heat transfer area of the test specimen. The cold mass also includes a copper edge guard ring that is completely and conveniently adjustable. This additional edge guard provides for additional thermal fine-tuning capability and expands the capability of the Cryostat-500 assembly by allowing testing of thicker specimens.

Figure 32:
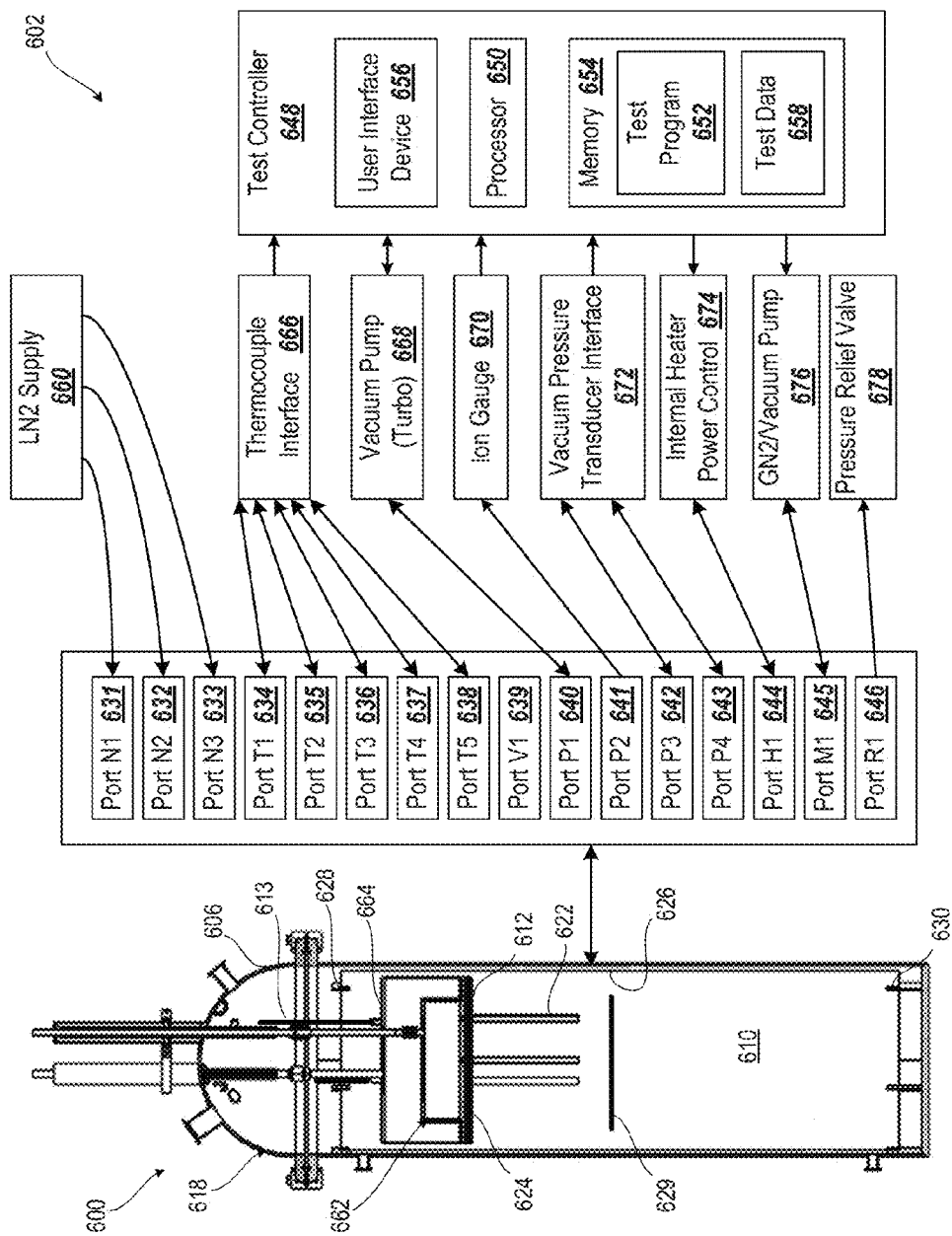
FIG. 32 illustrates a side, cross sectional view of the Cryostat-600 assembly of FIG. 31 in cross section along lines A-A and a functional block diagram of a testing system, according to one embodiment.

ASTM International's Committee C16 on Thermal Insulation has produced a new standard, ASTM C1774, *Standard Guide for Thermal Performance Testing of Cryogenic Insulation Systems*, that includes provision for the use of several types of insulation test cryostats including Cryostat-500. Another standard, ASTM C740, *Standard Guide for Evacuated Reflective Insulation In Cryogenic Service*, has also been updated. In order to obtain the thermal performance data related to these standards, the Cryostat-500 assembly is a primary candidate for performing these tests. The present invention offers the capability of testing high-performance materials performing at thermal conductivities below the 10 mW/m-K range and at conditions that are representative of actual-use. This range below 10 mW/m-K down to 0.1 mW/m-K (or even lower) is important for the newer materials on the market including aerogels and aerogel-based composites of all types. In addition, energy-efficiency standards are being increased worldwide and driving the need for higher performance materials as well as conventional materials that operate in a high-performance manner inside vacuum jacketed systems. Applications abound and include homes, commercial buildings, industrial processes, oil and gas, transportation, electrical power delivery, refrigerated shipping, food processing, handling of pharmaceuticals, and many others. Standard test methods on the market include ASTM C177 (guarded hot plate) and ASTM C518 (heat flux meter). The C177 gives absolute results when properly calibrated and executed. This sophisticated apparatus is expensive and may require years of experience to get adequate results under extreme conditions or for very low thermal conductivity values. The C518 is a lower cost instrument that only gives comparative results. This device is generally limited to near room temperature and ambient environment and cannot give suitable results for much beyond conventional, well-understood materials such as fiberglass board and polystyrene. The Cryostat-500 is suited for testing high performance materials or conventional materials. The Cryostat-500 has been demonstrated to provide consistent thermal conductivity data from below 0.1 mW/m-K up to 200 mW/m-K and is extremely practical to use over this wide range. While working in complementary fashion with the capabilities of the current instruments, the present invention is not limited to small temperature differentials but can easily provide large temperature differentials that are often more representative of the actual-use conditions of most materials and products. It The Cryostat-500 works in concert with Cryostat-100 (cylindrical, absolute), Cryostat-200 (cylindrical, comparative), and Cryostat-400 (flat plate, comparative) cryogenic testing devices. Cryostat-600. In FIGS. 28-32, the present invention is also directed to a guarded, two-dimensional flat plate calorimeter, hereinafter referred to as Cryostat-600 assembly 600 of a cryogenic testing system 602 may act as a boiloff calorimeter having a flat bottom support plate for measuring the absolute thermal performance of an insulation test article. The Cryostat-600 assembly 600 includes a vacuum chamber can 604 having vacuum chamber lid 606 overtop and clamped to it in a sealed state by eight (8) chamber lid clamps 608. FIG. 32 depicts an interior, sealable chamber 610 of the Cryostat-600 assembly 600 that contains a cold mass assembly 612 attached underneath the vacuum chamber lid 606 by compliance rods 613, two guard vessel feed tubes 614 and a test vessel feed tube 616 to form a vacuum chamber lid assembly 618. The feed tubes 614, 616 may be formed of 0.500" dia.×0.035" wall SST 304L tube. The vacuum chamber lid assembly 618 is positioned via support lugs 620 that extending laterally to lower the cold mass assembly 612 into the vacuum chamber can 604.

Figure 33:
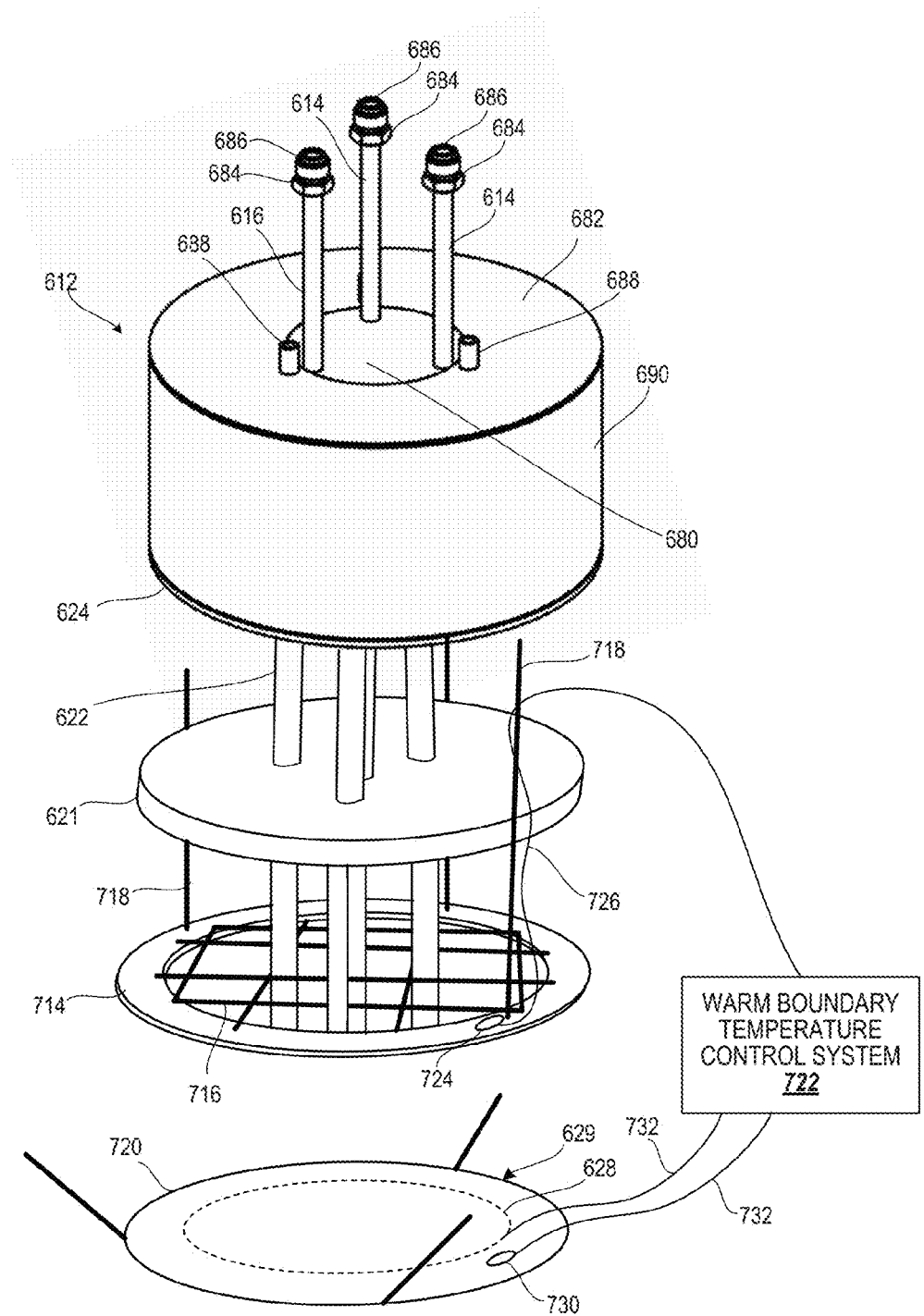
FIG. 33 is an isometric view of a cold mass assembly of the Cryostat-600 assembly of FIG. 32 with an exploded view of a test specimen, low thermal conductivity specimen support ring, and radiator plate assembly, according to one embodiment.

The cold mass assembly 612 is engaged from above to a test article 621 (FIG. 33). One or more penetrations rods 622 can be attached to a cold mass vessel bottom 624 of the cold mass assembly 612 to pass through the test article 621 and to extend downward into a portion of the interior, sealable chamber 610 that is heated by a cylindrical heater 626. The cold mass assembly 612 is suspended within the cylindrical heater 626 by three compliance rods 613. The cylindrical heater 626 in turn is suspended within the vacuum chamber can 604 by five evenly-spaced upper heater standoffs 628 and five evenly-spaced lower heater standoffs 630, each formed from 0.25" thick G-10 sheet. A passive or active radiator plate assembly 629 may be mounted within the sealable chamber and located at a distance below the lower surface of the test article 621.

Figure 28:
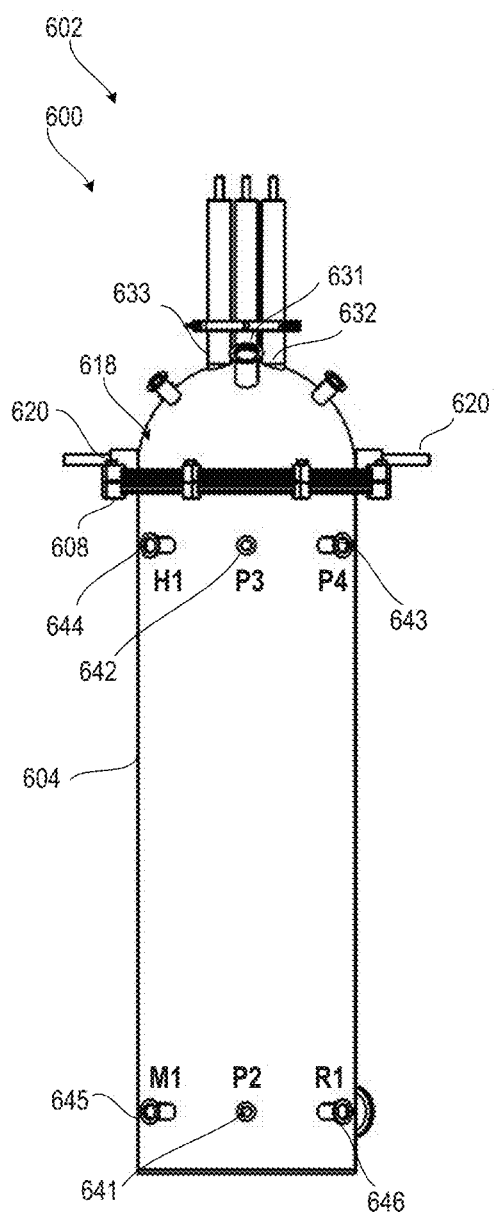
FIG. 28 illustrates a side view of a Cryostat-600 assembly, according to one embodiment.
Figure 29:
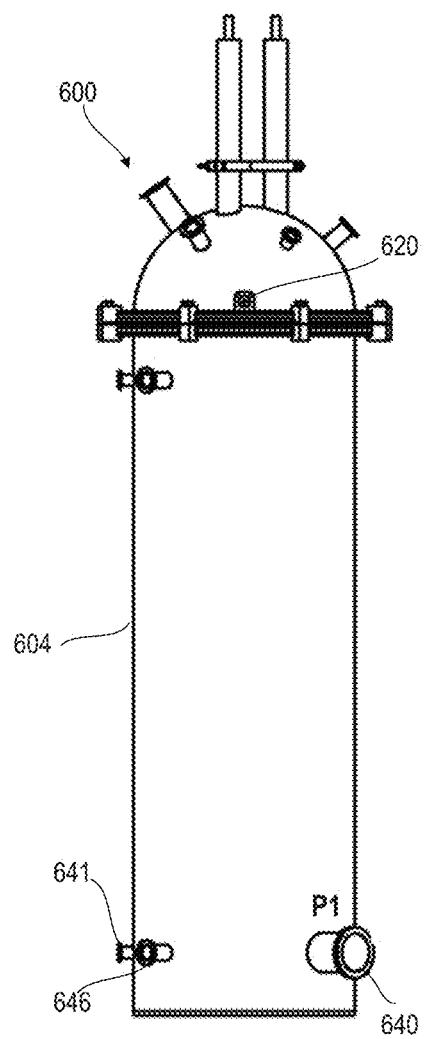
FIG. 29 illustrates a side view of the Cryostat-600 assembly of FIG. 28 from a further right vantage point, according to one embodiment.
Figure 30:
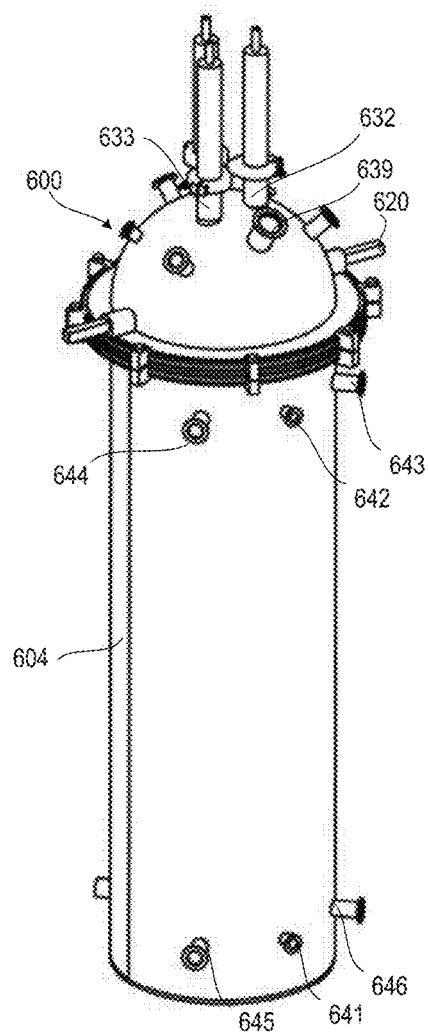
FIG. 30 illustrates a top isometric view of the Cryostat-600 assembly of FIG. 28 from a further left vantage point, according to one embodiment.
Figure 31:
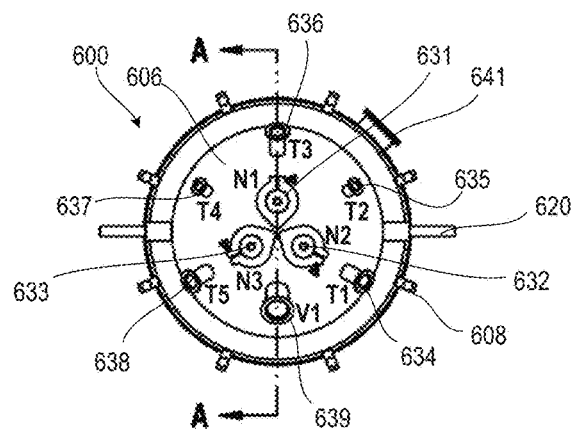
FIG. 31 illustrates a top view of the Cryostat-600 assembly of FIG. 28, according to one embodiment.

The Cryostat-600 assembly 600 in an exemplary embodiment includes four (one center and three peripheral) threaded ports in the bottom of the cold mass assembly 612 for mounting components, allowing for mounting of hardware to the bottom of the calorimeter to test real-life situations with non-ideal insulation. This configuration allows for testing insulation systems in relevant environments. Not only can large temperature differences be achieved across the insulation (approximately 300 K to 77 K) but it becomes possible to measure thermal performance degradation due to having non-ideal insulation and other structural components and system integrations that might otherwise adversely impact the insulation Ports provide access to an interior of the Cryostat-600 assembly 600 when the system is sealed. With particular reference to FIG. 30, ports N1 631, N2 632, N3 633, T1 634, T2 635, T3 636, T4 637, T5 638, and V1 639 pass through a vacuum chamber lid 606 of the vacuum chamber lid assembly 618. With particular reference to FIGS. 28-29, port P1 640, P2 641, P3 642, P4 643, H1 644, M1 645, and R1 646 pass through the vacuum chamber can 604. The ports 631-646 allow for dimensional heat transfer measurements throughout the insulation in the presence of structure or other variations in the simulation system. The ports 631-646 also allow for mounting hardware for cold shocking the hardware as a dual use of the cold mass assembly 612. This allows for the calorimeter (Cryostat-600 assembly 600) to be multifunctional and opens up another testing capability. The purpose of the respective ports 631-646 is introduced in TABLE 5 below:

TABLE 5

| PORT | REF | DESCRIPTION | SIZE (mm) |
|---|---|---|---|
| N1 | 631 | LN2 FILL, TEST VESSEL | 40 |
| N2 | 632 | LN2 FILL, GUARD VESSEL | 40 |
| N3 | 633 | LN2 FILL, GUARD VESSEL | 40 |
| T1 | 634 | 5-TYPE E THERMOCOUPLE | 25 |
| T2 | 635 | 5-TYPE E THERMOCOUPLE | 16 |
| T3 | 636 | 5-TYPE E THERMOCOUPLE | 25 |
| T4 | 637 | 5-TYPE E THERMOCOUPLE | 16 |
| T5 | 638 | 5-TYPE E THERMOCOUPLE | 25 |
| V1 | 639 | VIEW PORT | 40 |
| P1 | 640 | VACUUM PUMP (TURBO) | 63 |
| P2 | 641 | ION GAUGE | 16 |
| P3 | 642 | VACUUM/PRESSURE TRANSDUCER (PFEIFFER) | 16 |
| P4 | 643 | VACUUM/PRESSURE TRANSDUCER (MKS) | 25 |
| H1 | 644 | HEATER CONNECTION | 25 |
| M1 | 645 | GN2 & VACUUM PUMPING | 25 |
| R1 | 646 | 15 psig (MAX) RELIEF VALVE | 25 |

A test controller 648 is connected with the Cryostat-600 assembly 600 to form the cryogenic testing system 602. The test controller 648 interfaces to one or more of the aforementioned active components to sense values, and to control a testing procedure than can be executed by one or more processors 650 as a test program 652 in memory 654. The test controller 648 can respond to user inputs via a user interface device 656 and can record test data 658 for later analysis and test reporting. For example, the test program 652 may perform a method of testing of materials and thermal systems using boiloff calorimetry where absolute thermal performance measurements are enabled by complete thermal guarding of a cylindrical measurement vessel and the edge of a round disk type test specimen. In a particular aspect, the test program 652 may require or control a filling process of both the test vessel and the guard vessel wherein liquid levels are manipulated to provide complete thermalisation and elimination of adverse heat effects from the edge boundary. Alternatively, the test program 652 may obtain absolute thermal performance measurements of a structural test specimen such as a tube, strut, pipe, bar, or other element that is physically attached and thermally anchored to the lower surface of the test vessel.

An LN2 supply 660 provides LN2 to Port N1 631 for a test vessel 662 of the cold mass assembly 612. The LN2 supply 660 provides LN2 to Port N2 632 for a guard vessel 664 of the cold mass assembly 612. The LN2 supply 660 provides LN2 to Port N3 633 also for the guard vessel 664. Port T1 634 provides access for a thermocouple interface 666 coupled to the test controller 648 to monitor a 5-type E thermocouple positioned within the interior, sealable chamber 610. Port T2 635 provides access for the thermocouple interface 666 to monitor a S-type E thermocouple positioned within the interior, sealable chamber 610. Port T3 636 provides access for the thermocouple interface 666 to monitor a 5-type E thermocouple positioned within the interior, sealable chamber 610. Port T4 637 provides access for the thermocouple interface 666 to monitor a 5-type E thermocouple positioned within the interior, sealable chamber 610. Port T5 638 provides access for the thermocouple interface 666 to monitor a 5-type E thermocouple positioned within the interior, sealable chamber 610. Port V1 639 enables viewing into the vacuum chamber lid 606. Port P1 640 pneumatically communicates with a vacuum pump (turbo) 668. Port P2 641 communicates with an ion gauge 670. Port P3 642 provides access to a vacuum pressure transducer positioned in the interior, sealable chamber 610 by a vacuum pressure transducer interface 672 that is coupled to the test controller 648. Port P4 643 provides access to a vacuum pressure transducer positioned in the interior, sealable chamber 610 by the vacuum pressure transducer interface 672. Port H1 644 provides access between the cylindrical heater 626 and an internal heater power control 674. Port M1 645 provides access to the interior, sealable chamber 610 for a GN2 insertion and for a vacuum pump 676. Port R1 646 pneumatically communicates with a pressure relief valve 678 (15 psig).

Figure 34:
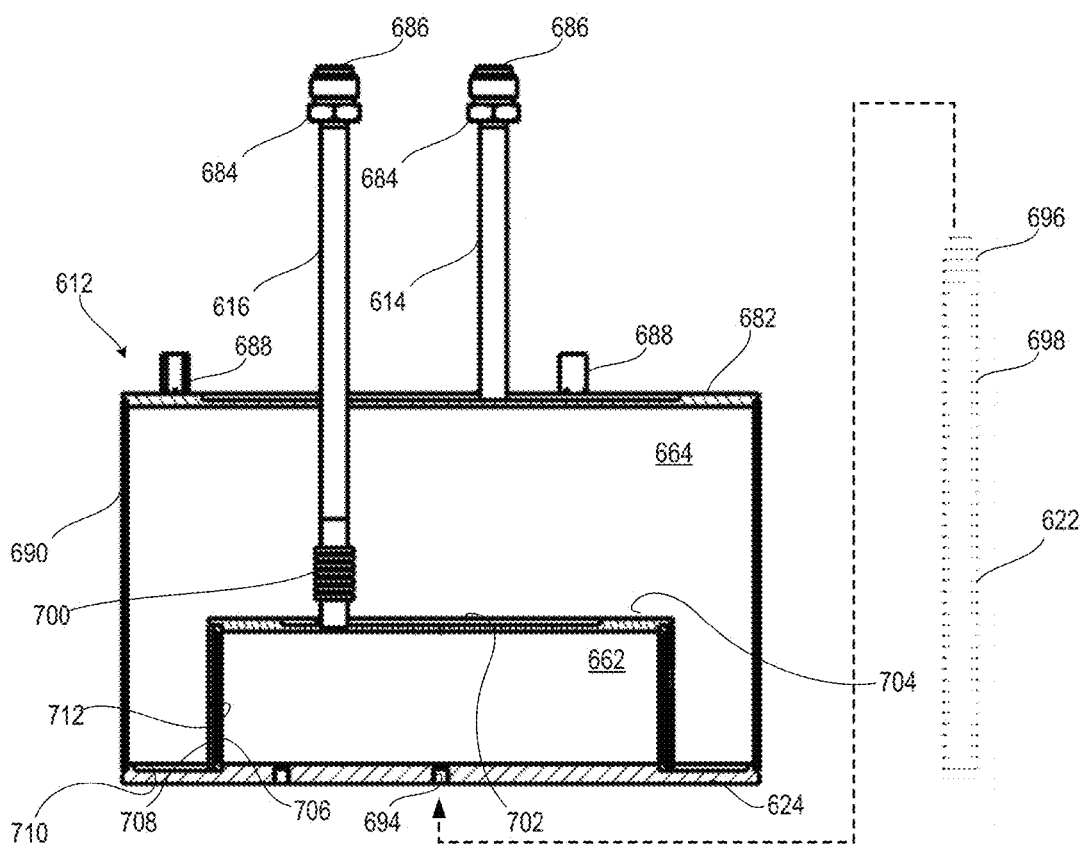
FIG. 34 is a side view of the cold mass assembly of FIG. 33 in cross section, according to one embodiment.
Figure 34A:
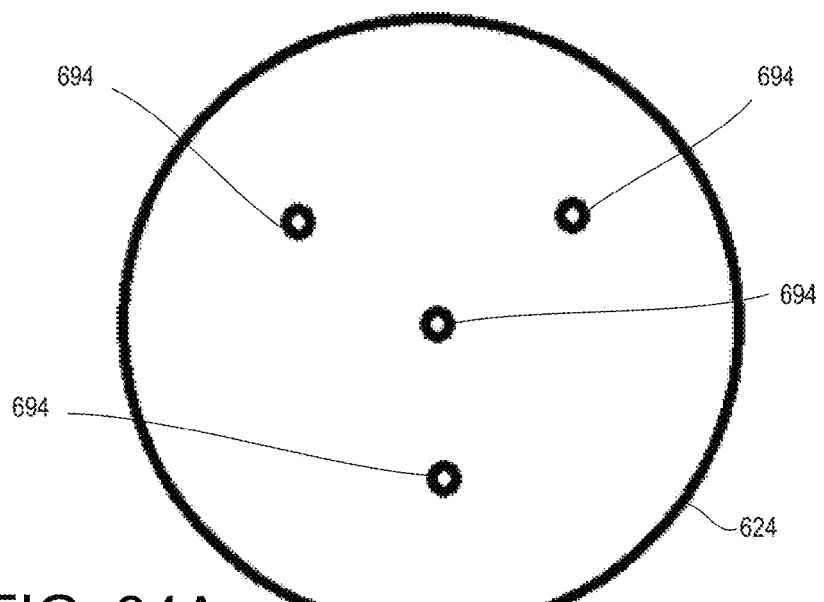
FIG. 34A illustrates a bottom view of a cold mass assembly of the Cryostat-600 assembly of FIG. 32.

FIGS. 33-34 illustrates the cold mass assembly 612. The two guard vessel feed tubes 614 and the test vessel feed tube 616 pass through a central circular recess 680 of a guard vessel top 682 and each include a welded male tube fitting 684 and a welded tube end 686. Three cold mass support bosses 688 spaced on the guard vessel top 682 are provided for structurally supporting the cold mass assembly 612. The guard vessel 664 is laterally enclosed by a guard vessel wall 690, that may be 0.090" thick of SST 304L sheet. With particular reference to FIGS. 34-34A, in an exemplary embodiment the cold mass vessel bottom 624 includes threaded ports 694 for attaching penetration rods 622, which may be formed from a penetration rod insert 696 (0.500× 0.70 aluminum 6061 round bar) attached to penetration rod tube 698 (0.500" dia.×0.063" wall G-10 glass laminate tube). The test vessel feed tube 616 has a bottom end attached to a flexible tube 700 that communicates with the test vessel 662 through a central circular recess 702 in a test vessel top 704 (0.250" thick SST 304L plate). In FIG. 34, lower ends of test vessel inner and outer walls 706, 708 of the test vessel 662 reside in an upwardly presented annular recess 710 in the cold mass vessel bottom 624. A thermal break is provided by a condensable vapor pocket 712 or void space between the test vessel inner and outer walls 706, 708 are purged with $CO_2$ gas via a threaded boss in the center of the cold mass vessel bottom 624. A ⅛" NPT plug then closes the threaded boss and is seal welded to the outer wall of the test vessel 662 to retain the $CO_2$ gas. Other gases such as argon may be used depending upon the temperatures being tested.

FIG. 33 further illustrates support for the test article 621 and the radiator plate assembly 629 mounted within a sealable chamber 610 and located at a distance below the lower surface of the test specimen 621. For example, the test specimen 621 may be suspended from the bottom of the cold mass assembly 612 on a low thermal conductivity specimen support ring 714 that is laced by a plurality of horizontal support strings 716 and suspended by three or more support strings 718 to attach points on the upper surface of the cold mass assembly 612.

In one embodiment the radiator plate assembly 629 is passive with a metal plate 720 of a diameter approximate to that of the test specimen 621 and coated on an upward surface with a high emissivity material. A warm boundary temperature control system 722 may monitor a resulting temperature detected by one or more temperature sensors 724 embedded in the specimen support ring 714 with lead wires 726 that follow the support strings 718.

In one embodiment, the radiator plate assembly 629 is active with an electrical heater 628. In addition, one or more temperature sensors 730 may be embedded in the metal plate 720 with leads 732 connected to the warm boundary temperature control system 722. The warm boundary temperature control system 722 may be used to heat the longitudinal lower end of the test specimen 621 to a fixed warm boundary temperature and the steady-state heat conduction along the length of the test specimen 621 is measured by the heat transmission to the test vessel.

Typical dimensions of the Cryostat-600 assembly 600 allow for testing test specimen or article 621 up to approximately 300 mm in diameter by up to approximately 30 mm in thickness. Struts (penetrations 622) may be approximately 300 mm in length. Various solid or hollow tubes may be placed throughout the insulation to create two-dimensional heating effects, especially adaptable for use with anisotropic materials using four threaded ports 694 machined into the bottom of the calorimeter. Temperature sensors may be located on one or more sides of the apparatus in addition to the boundary temperatures throughout the test specimen. Useful test information may also be obtained for struts themselves without a particular insulative test specimen being present.

The test chamber of the Cryostat-600 assembly 600 is guarded by a second cryogenic chamber to prevent parasitic head loads not through the measure insulation system. System insulation materials provide additional thermal stability for testing over a wide range of environmental conditions. The system is capable of achieving any vacuum between ambient pressure and approximately $10^{-7}$ torr. Heaters internal and external to the vacuum chamber control the environmental temperature of the test device.

The Cryostat-600 assembly 600 provides a wide range of heat-flux performance over the full range of environmental conditions including vacuum levels from approximately $10^{-7}$ to approximately $10^{+3}$ torr. The instrument has been proven through extensive testing of multilayer insulation (MLI) systems with metallic penetrations. The thermal data quality and quantity has increased as more testing is completed. The Cryostat-600 assembly provides the steady state thermal performance measurements of insulation materials at various degrees of actual insulative value, from ideal to highly degraded states.

Thermal insulation systems may comprise one or more specimen that may be homogeneous or non-homogeneous at boundary conditions ranging from approximately 4 K to 400 K and in environments from high vacuum to ambient pressure of residual gas.

The testing methods are distinct from, and yet complementary to, other ASTM thermal testing methods. The cold boundary temperature can be varied at discrete points between approximately 4 K and 80 K with the warm boundary temperatures between approximately 280 K and 350 K, depending on the vacuum level. The vacuum level can be changed between approximately $10^{-7}$ torr and approximately $10^3$ torr, covering all vacuum ranges and environments using various background gases.

Over the full range of vacuum-pressure levels, the thermal performance can vary by several orders of magnitude of heat loads. Although the high performance evacuated insulation systems in this configuration are not currently covered by existing ASTM test methods, they are, nevertheless, of great interest. The present invention includes handling tools, instrumentation, methodology, data acquisition (hardware and software), and other ancillary equipment needed to provide consistent test results in a cost-effective, safe, and reliable manner.

The Cryostat-600 assembly 600 is adaptable to be fit within the Cryostat-100 vacuum chamber and to be handled by the same lifting equipment, allowing data acquisition for each calorimeter to be run off the same control program. This allows for interchanging of the calorimeters if needed.

The Cryostat-600 assembly 600 is adaptable to testing exotic, high-performance materials or conventional materials with equal ease. The Cryostat-600 assembly is not limited to small temperature differentials like other known apparatus, but can easily provide large to very large temperature differentials which are more representative of the actual use conditions of most materials and products. The four threaded ports allow for cold sinking nearly anything that will fit within its vacuum chamber. Due to the guarded structure of the present invention, the cold soaks could even be done with liquid helium as low as approximately 4 K.

The remaining material of the present disclosure is further descriptive information of the structure and experimental testing of the present invention according to one embodiment.

NASA and other space-related agencies and institutions have long cited long duration storage of cryogenic propellants in space as a major technological hurdle for future exploration. No matter what the application, long duration storage requires the minimization of energy being transmitted into the cryogenic tank from all sources. For propulsion applications, the most efficient fuel is liquid hydrogen. With a normal boiling point of 20 K, hydrogen has the second lowest boiling point of all fluids and it also has the lowest density at normal boiling point of all fluids. This combination makes the storage of large quantities of hydrogen much more difficult than other fluids. High performance insulation systems are required for the long duration storage of liquid hydrogen. Multilayer Insulation (MLI), with the proper selection of materials, methodologies, and approach provides the potential for the best thermal performance among all insulation systems. Similar technology goals apply for the storage of LH2 or liquefied natural gas (LNG) [112 K] for ground transportation (cars, trucks, trains), aircraft and ships.

Experimental Test Results for C-500 Assembly

Introduction: Four Load Bearing Multilayer Insulation (LB-MLI) test specimens were tested on Cryostat-100 assembly (C-100). Two more test specimens were then procured for testing on Cryostat-600 assembly (C-600). The test specimens are described in general in TABLE 6. All test specimens had a layer density of approximately 0.5 layers/mm.

TABLE 6

General Description of LB-MLI thermal testing test specimens

| Test Specimen Name | Number of Layers | Perforated? | Calorimeter | Geometry |
|---|---|---|---|---|
| A | 5 | No | C-100 | Cylindrical |
| B | 10 | No | C-100 | Cylindrical |
| C | 10 | Yes | C-100 | Cylindrical |
| D | 20 | No | C-100 | Cylindrical |
| F | 18 | No | C-600 | Flat Plate |
| G | 18 | No | C-600 | Flat Plate |

Test specimens F and G were further tested to understand the impact of penetrating the LB-MLI blankets with structural, fluid, or electrical penetrations. Both Cryostat-600 test specimens were specified as circular disks with an outer diameter of 300 mm. All holes for the penetrations were punched into the test specimens at KSC after the test specimen was first tested without a hole. The test specimens consisted of 18 layers and were tested in the Cryostat-600 assembly to measure the change in heat load experienced due to the presence of a penetration through the LB-MLI. The Cryostat-600 test matrix is shown in TABLE 7. Three different penetrations were used, all made of standard Aluminum 6061-T6 tubes (0.25" OD by 0.035" wall, 0.5"×0.032", and 1.0"×0.049") with a welded end cap.

TABLE 7

Cryostat-600 Test Matrix

| Test Series | Specimen | Strut Size (in) | Cryolite Thickness (in) | Notes |
|---|---|---|---|---|
| P130 | F | N/A | N/A | Baseline heat load for future measurements |
| P131 | F | 0.25 | 0.25 | Quarter inch strut, thickness based on change in radius |
| P132 | F | 0.5 | 0.25 | Half inch strut |
| P133 | F | 0.5 | N/A | Removed Cryolite to test vacuum buffer |
| P134 | F | 0.5 | 0.5 | Slightly enlarged hole size |
| P135 | F | 1.0 | 0.5 | One inch strut |
| P136 | G | N/A | N/A | Repeat Baseline heat load on second test article |

Test Results: Testing on Cryostat-100 assembly was completed, as well as testing on Cryostat-600. A summary of all test results are given in Table 8 for Cryostat-600 assembly, Q is for heat flow and A is for area, thus Q/A is heat flux.

TABLE 8

Test Results from Cryostat-600 Assembly Testing

| Test # | Test Configurations | Flow/Vdot (sccm) | Qtot (W) | Open (W) | Vacuum Pressure (Torr) | WBT (K) | Q/A (W/m$^2$) | Punch Diameter (in) | Q MLI | delta Q |
|---|---|---|---|---|---|---|---|---|---|---|
| P130 | IMLI Specimen F - No Penetration | 28.3 | 0.117 | 0 | 7.01E−04 | 297.3 | 3.41 | 0 | 0.117 | 0.000 |
| P131 | IMLI - 0.25" strut, 0.5" cryolite | 153.9 | 0.637 | 0.402 | 6.10E−04 | 296.3 | 18.56 | 12/16 | 0.235 | 0.118 |
| P132 | IMLI - 0.5" strut, 0.5" cryolite | 702.8 | 2.908 | 2.043 | 6.03E−04 | 297.1 | 84.73 | 1 | 0.865 | 0.748 |
| P133 | IMLI - 0.5" strut, vac buffer | 709.7 | 2.937 | 2.69 | 1.85E−03 | 297.3 | 85.58 | 1 | 8/16 | 0.247 | 0.130 |
| P134 | IMLI - 0.5" strut, 1" cryolite | 610.8 | 2.528 | 2.11 | 6.85E−04 | 296.9 | 73.66 | 1 | 8/16 | 0.418 | 0.301 |
| P135 | IMLI - 1.0" strut, 0.5" cryolite | 1501 | 6.212 | 5.85 | 1.12E−03 | 297.4 | 181.00 | 2 | 0.362 | 0.245 |
| P136 | IMLI Specimen G - No Penetration | 37.6 | 0.148 | 0 | 4.45E−04 | 297.1 | 4.31 | 0 | 0.148 | 0.031 |

Cryostat-600 Assembly Testing: Testing on Cryostat-600 assembly was done using the Cryolite material previously chosen as the best material for isolating penetrations from the MLI. (3) Three different sized penetrations were used: 0.25", 0.5", and 1.0." In all cases, the LB-MLI tested equal or better than the traditional MLI. While the traditional MLI had slightly more layers (25 to 18), the LB-MLI was much thicker (1.4" to 0.5"), this makes comparisons between the two to be tedious at best. No temperature degradation along the LB-MLI layers was noticed, although due to the prefabricated nature of the LB-MLI blanket, it was hard to place thermocouples within the blanket on precise layers.

Cryostat-600 assembly has four threaded ports in the bottom of the cold mass for mounting components, this allows for mounting hardware to the bottom of the calorimeter to test real life situations with non-ideal insulation. The ports allow for two dimensional heat transfer measurements through the insulation in the presence of structure or other variations in the insulation system. This plays into testing insulation systems in relevant environments. Not only can large temperature difference across the insulation be used (300 K to 77 K), but the present invention can measure degradation due to having non-ideal insulation and other systems that might impact the insulation. The test setup is designed to be large enough to see the edge of the degraded area.

These ports also allow for mounting hardware for cold shocking the hardware as a dual use of the cold mass. This allows the calorimeter to be multifunctional and opens up another capability for the laboratory.

In use of the Cryostat-500 and Cryostat-600 assemblies, one valuable technique for testing the thermal performance of materials, such as insulation material, is evaporation or boiloff testing. Boiloff testing is accomplished by filling a vessel with a fluid which evaporates or boils below ambient temperature. In the general sense, boiling is associated with higher heat transfer rates and evaporation with lower heat transfer rates. Although the exemplary fluid is the cryogen liquid nitrogen, other fluids such as liquid helium, liquid methane, liquid hydrogen, or known refrigerants may be used. A vessel is placed against testing material, placed in a suitable environmental chamber, and then filled with the test fluid such as a cryogenic liquid. A calorimetry method is then used to determine the thermal conductivity of the test material by first determining the rate of heat passing through the test material to the vessel containing the refrigerant liquid. The heat leakage rate passing through the test material to the liquid in the vessel is directly proportional to the liquid boiloff rate from the vessel. For a test material under a set vacuum pressure, the effective thermal conductivity ($k_e$) and/or heat flux is determined by measuring the flow rate of boiloff at prescribed warm and cold boundary temperatures across the thickness of the sample.

Although other cryogenic boiloff techniques and devices have been prepared to determine the thermal conductivity of insulation material, the previous techniques and devices are undesirable for a variety of reasons. First, few such cryogenic devices are in operation because of their impracticality from an engineering point of view. The previous boiloff devices made it extremely difficult to obtain accurate, stable measurements and required extremely long set up times. Prior testing devices also needed highly skilled personnel that could oversee the operation of the testing device for extended periods of time, over 24 hours to many days in some cases. Additionally, constant attention was required to operate previous testing devices to make the necessary fine adjustments required of the testing apparatus. The testing of high-performance materials such as multilayer insulation requires extreme care in fabrication and installation. Localized compression effects, sensor installation, and outgassing are further complications. Measurements of various testing parameters were not carefully determined or controlled in previous testing devices. Measurement of temperature profiles for insulation material was either not done or was minimal because of the practical difficulties associated with the placement, feed-through, and calibration of the temperature sensors. Vacuum levels were restricted to one or two set points or not actively controlled altogether. Previous cryogenic testing devices required complex thermal guards having cryogenic fluid-filled chambers to reduce unwanted heat leaks (end effects) to a tolerable level. The previous technique for providing thermal guards, filling guard chambers with the cryogen, caused much complexity both in construction and operation of the apparatus. Known techniques add the further complication of heat transfer between the test chamber and the guard chambers due to the thermal stratification and destratification processes of the liquid within the chambers.

Figure 35:
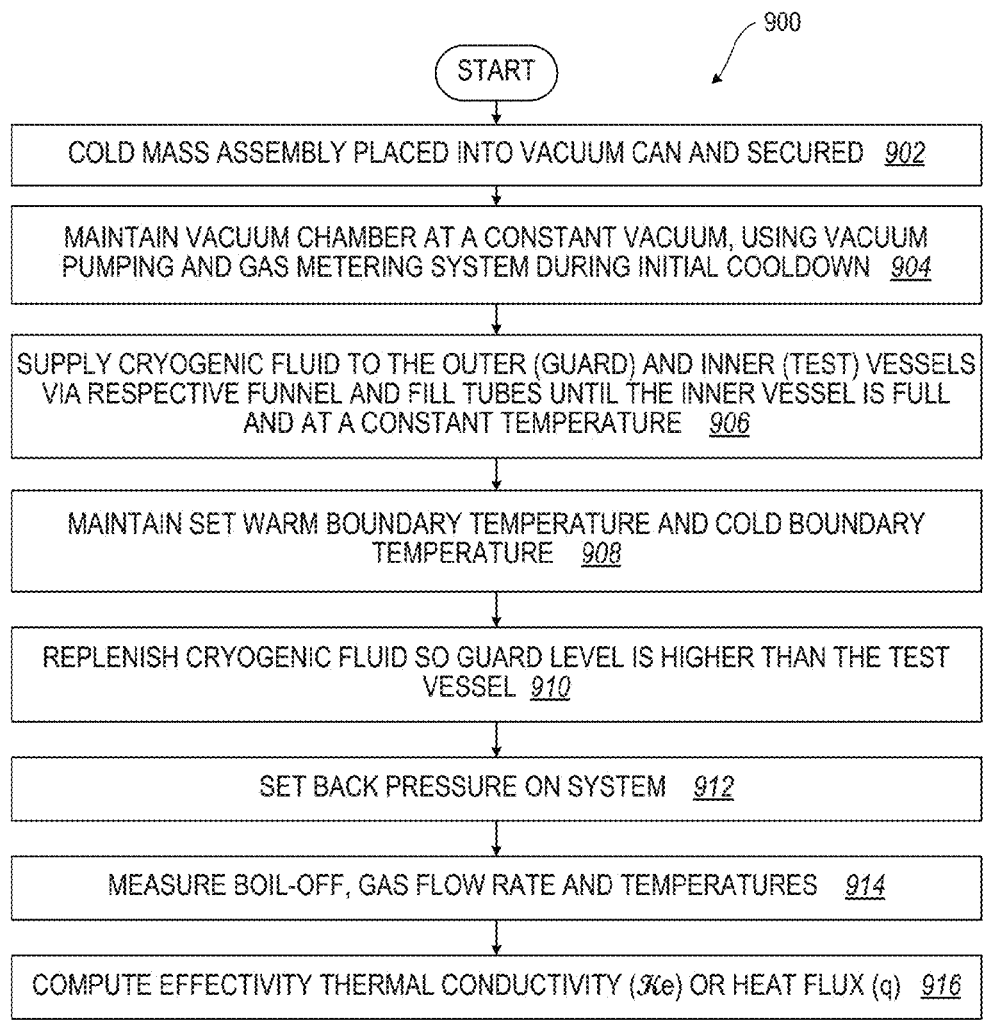
FIG. 35 illustrates a flow diagram of a methodology for testing disk-shaped articles, according to one embodiment.

FIG. 35 illustrates a method 900 for testing disk-shaped test articles. Once the cold mass assembly is secure with the test specimen, the vacuum chamber is sealed (block 902), the cryogenic fluid is supplied to vessels via respective funnel and fill tubes, until the inner vessel is full and at a constant temperature (block 906). The vacuum chamber is maintained at a constant vacuum, using an exemplary vacuum pumping and gas metering system (block 904), and a set sidewall temperature, using a preferred electrical heater system (block 908).

The temperature differential between the cold boundary temperature and the warm boundary temperature of the testing material is measured by the temperature sensors and these values, along with the boiloff flow rate and the material thickness, are used to compute the $k_e$ (blocks 914 and 916). While calibration of the device is not required, verification of zero heat leak rates through the ends, or "end effects" can be accomplished by testing a material with a known thermal conduction properties under the pressure and temperature conditions of interest.

For example, thermal energy management is provided for cryogenic boiloff, cylindrical absolute thermal performance testing of a disk-shaped test article, optionally with a strut penetration. The Cryostat-500/600 apparatus is provided with a vacuum chamber having ports to accommodate funnel-type filling system with two (2) or three (3) feedthroughs (pairs of feedthroughs), capable of the combination of filling and venting of both chambers. There are temperature sensors (e.g., 15 pairs of thermocouple lead wire conductors), a viewing port, and auxiliary ports for additional instrumentation. The cold mass is supported by strings or thin wires to minimize heat transfer from the lid. A thermal break (narrow vertical void space with condensable gas) is provided between inner and outer chambers to eliminate heat transfer from the circumferential edge into the test chamber. A cold edge guard is also provided for further fine adjustment and calibration or to facilitate the testing of thicker test specimens, such as thicker than 1-inch, or the testing at extremely low levels of heat flux. Cold edge guards comprised of copper, aluminum, or engineering polymer have been used. Materials of the test specimen may be isotropic, multi-layered, composites, or any combination of dissimilar materials.

An exemplary embodiment is of stainless steel construction with the integral thermal break that provides independently stratified (not mixed) liquid condition in both chambers. Each chamber has a stratified vertical column of liquid and these stratified columns are further independent of one another. Thereby, the prior art problems associated with heat exchange between chambers and with re-condensation of test chamber boiloff vent gas are avoided. Ultra-critical chamber pressure regulation and complex control systems, required in the prior art of boiloff testing, is completely eliminated by the Cryostat-500 and Cryostat-600 designs. At very low heat flux levels, the daily cyclic variations in barometric pressure can cause a similar cyclic pattern in the boiloff test result. But this effect is eliminated or minimized by discharging all three vent flows into a common reservoir surge vessel that is maintained at a slightly higher pressure above the prevailing room pressure (a delta pressure of approximately 4 millibar is sufficient for most locations). Back pressure regulation is generally required for very low heat transfer rate testing and is generally unnecessary for medium to high heat transfer rate tests.

With continued reference to FIG. 35, during operation of the Cryostat-500/600 apparatus the cold mass assembly is secured in the vacuum can (block 902). Vacuum canister temperature and vacuum levels are maintained during initial cool down and subsequently during cold soak (block 904). Two chambers are cooled and then filled with liquid nitrogen (LN2), liquid hydrogen (LH2), liquid helium (LHe), or other cryogens or liquid refrigerants. The vessels are allowed a period of thermal stabilization after the cooling and filling process is complete (block 906). During an operational testing period, a set warm boundary temperature may be controlled while the cold boundary temperature is fixed by the saturated condition of the liquid inside the chambers (block 908). In an exemplary embodiment, each chamber is filled and vented through a respective feedthrough funnel tube assembly with cryogenic fluid being replenished so that the guard level is higher than the test vessel (block 910). Back pressure is set for the system (block 912). The boiloff gas flow rate, and temperatures are measured (block 914). These values, along with the material thickness, are used to compute effective thermal conductivity ($k_e$) or heat flux (q) values (block 916).

Initial cool down of the cold mass assembly is achieved in approximately one to two hours. Complete cool down, liquid filling, and thermal stabilization through the thickness of the insulation test specimen may require from 1 to 100 hours or perhaps more depending on the level of thermal performance of the test specimen. It should be appreciated that quick duration tests can also be performed to achieve good data, although the results may not be necessarily certified against prior tests or standard reference data. During cool down and stabilization, chambers are replenished as necessary to maintain them approximately full. Liquid levels may range from approximately half full to full without compromise to the success of the cool down and stabilization phase. During operational testing, the guard and test chambers may be allowed to be nearly empty. Preferably, the guard chamber is maintained at a level that is at least enough to cover the top of the test chamber. Temperature sensors may be installed throughout the cold mass assembly to monitor conditions during the cooling, filling, and refilling operations. In one example, thermocouples made of 30-gage Type E wire in approximate one meter lengths are affixed on the outside surface of the guard chamber side wall to gauge the liquid level. Alternatively, the flow meter outputs for both guard and test chambers can be totalized by computer analysis to give real-time estimates of the liquid level inside each chamber. The thermal break between the chambers allows flexibility in operations regarding the level of liquid inside the test chamber. This design and method eliminates the problem in the prior art for careful and difficult maintaining of specific fill levels within the chambers for the duration of the test. Such filling and re-filling required by the prior art is made extraordinarily difficult by the fact that any newly added liquid will likely disturb the thermal equilibrium of the chambers and therefore extend the test duration or render the test invalid. For instance, the floor of the guard chamber may be below the floor of the test chamber and have sufficient cryogenic fluid to maintain cooling to compensate for edge effects even though the test chamber is allowed to boil off completely. Boiloff flow rates for both chambers are continuously monitored during this time by maintaining connection via flexible plastic tubing to the three mass flow meters. The level of back-pressure on the chambers, while not critical to the operation, must be maintained consistently and similarly for both chambers. The similar back-pressures are achieved simply by keeping all (two or three) connecting tubes (inner diameter and length), connecting hardware, and flow meter types the same. These flows may be further connected to a single reservoir to singularly and simultaneously regulate the back-pressure on all the liquid chambers so that periodic atmospheric pressure variations are either eliminated or minimized to an acceptable level. It should be noted that the back-pressure control is generally only necessary at very low heat flux values such as less than 1 $W/m^2$ or up to approximately 10 $W/m^2$.

During testing, operational sequences may be summarized as including:
(1) Heating and vacuum pumping;
(2) Liquid nitrogen cooling;
(3) Liquid nitrogen filling;
(4) Cold soak (thermal stabilization);
(5) Steady-state boiloff; and
(6) Warm up and purging.

While test operations utilizing the Cryostat-500/600 may be lengthy in duration, the actual operation of the Cryostat-500/600 apparatus requires little operator intervention. Consequently, production of new engineering data and scientific information is much more cost effective. The design of the Cryostat-500/600 apparatus is fully modular, portable, repeatable, and adaptable to different fluids or environmental test conditions. The Cryostat-500/600 apparatus is particularly well suited for testing a wide variety of materials. The device is easily adapted to utilizing different boundary temperatures up to 400 K and any cold boundary temperature above 77 K when using liquid nitrogen as the test liquid. Minor adaptations in material selection and facility details can allow cold boundary temperatures of 20 K (liquid hydrogen) or 4 K (liquid helium). The data obtained from utilization of the Cryostat-500 and 600 apparatus is to a level of accuracy that it creates standard reference material for the calibration of conventional insulation test equipment. Other cold boundary temperatures could be designed for 216 K (carbon dioxide), 246 K (Freon R134a), 351 K (ethyl alcohol), and other known refrigerants with suitable boiling points and latent heats of vaporization. Further adaptations of the present invention could enable the use of water (373 K) as the boiloff liquid.

Figure 36:
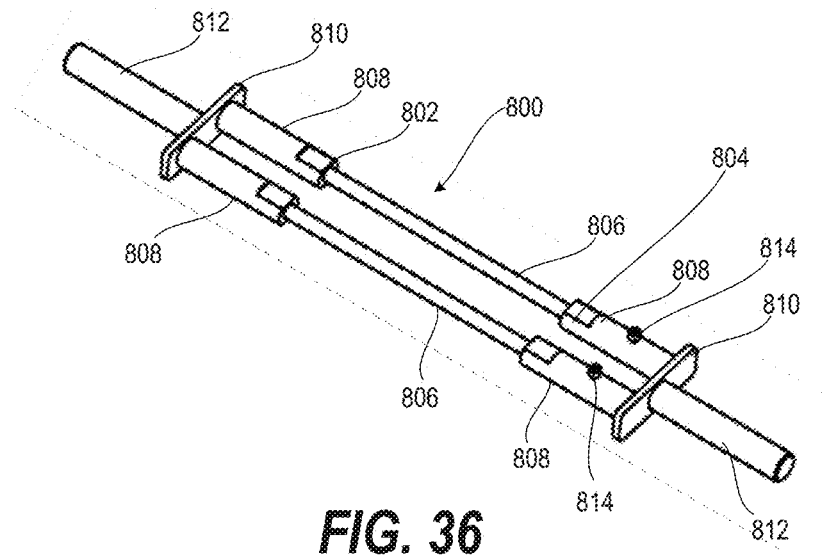
FIG. 36 illustrates an isometric view of a lifting tool for the cold mass assembly, according to one embodiment.

FIG. 36 illustrates a lifting tool 800 for lifting a cold mass assembly and includes left and right handle weldments 802, 804 connected by parallel support rods 806 received within opposing bores. Each handle weldment 802, 804 includes two support bosses 808 attached to a handle plate 810, which in turn is attached to a handle 812. The parallel support rods 806 are permanently attached within the two support bosses 808 of the left handle weldment 802 and releasably engaged with the right handle weldment 804 by socket head machine screws 814.

Figure 37:
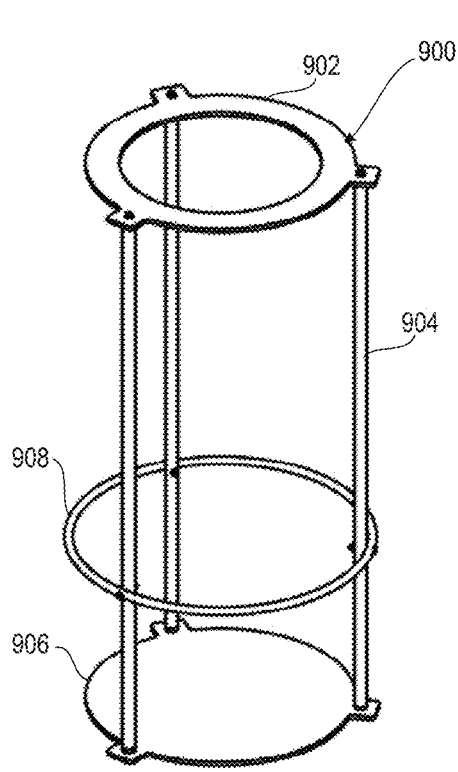
FIG. 37 illustrates an isometric view of a work stand, according to one embodiment.

FIG. 37 illustrates a first work stand 900 for supporting a cold mass assembly. A top plate 902 is attached at a top of three leg tubes 904, which in turn are attached at their bottom to a bottom plate 906. A hoop support tube 908 encompasses and is attached to the three leg tubes 904.

Figure 38:
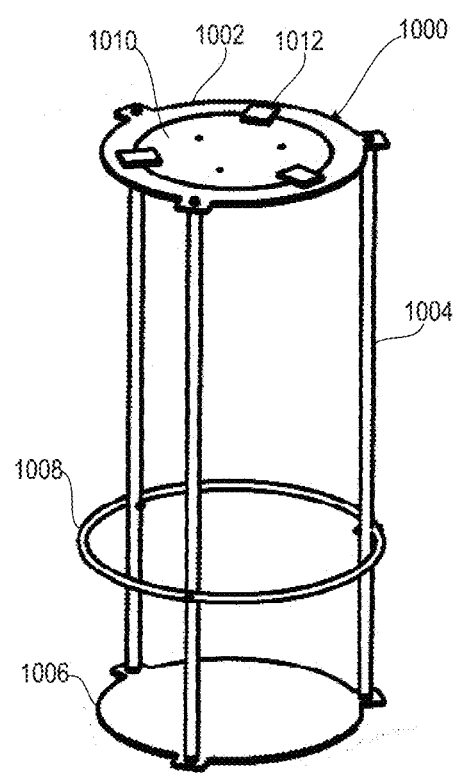
FIG. 38 illustrates an isometric view of an alternative work stand, according to one embodiment.

FIG. 38 illustrates a second work stand 1000 for supporting a cold mass assembly. A top plate 1002 is attached at a top of three leg tubes 1004, which in turn are attached at their bottom to a bottom plate 1006. A hoop support tube 1008 encompasses and is attached to the three leg tubes 1004. The top plate 1002 is filled by a hanger plate 1010 which are attached by three hanger plate weldments 1012.

For clarity, certain components described herein are formed from a low thermal conductivity material to reduce heat transfer from an exterior of the system to the test vessel 662 (FIG. 34). Certain components may also be formed from a high thermal conductivity material to rapidly reach equilibrium as part of cold soaking or operational testing to speed measurements. For example, the test specimen support ring 714 of FIG. 33 may be formed of either low or high thermal conductivity material.

By virtue of the forgoing, the present disclosure provides for a method of testing of materials and thermal systems using boiloff calorimetry where absolute thermal performance measurements are enabled by complete thermal guarding of a cylindrical test vessel and the edge of a round disk type test specimen. The filling processes of both the test vessel and the guard vessel are managed and liquid levels are manipulated to provide complete thermalisation and elimination of adverse heat effects from the edge boundary. The integral thermal break between the chambers provides decoupling of the thermal influence from one chamber to the other, thus enabling flexibility and simplicity in the operation of the test instrument in regard to liquid levels and re-filling processes through the duration of a test.

In certain embodiments, the method of testing of materials and thermal systems uses boiloff calorimetry where absolute thermal performance measurements are enabled by complete thermal guarding of a cylindrical test vessel and the side of a structural test specimen such as a tube, strut, pipe, bar, or other element that is physically attached and thermally anchored to the lower surface of the test vessel. For example, the longitudinal lower end of the test specimen may be heated to a fixed warm boundary temperature and the steady-state heat conduction along the length of the test specimen is measured by the heat transmission to the test vessel. Alternatively, the longitudinal lower end of the test specimen is subjected to sudden heat load and the transient heat conduction along the length of the test specimen is measured by the resulting heat transmission to the test vessel.

In the above described flow chart (FIG. 35), one or more of the methods may be embodied in a computer readable device containing computer readable code such that a series of functional processes are performed when the computer readable code is executed on a computing device. In some implementations, certain steps of the methods are combined, performed simultaneously or in a different order, or perhaps omitted, without deviating from the scope of the disclosure. Thus, while the method blocks are described and illustrated in a particular sequence, use of a specific sequence of functional processes represented by the blocks is not meant to imply any limitations on the disclosure. Changes may be made with regards to the sequence of processes without departing from the scope of the present disclosure. Use of a particular sequence is therefore, not to be taken in a limiting sense, and the scope of the present disclosure is defined only by the appended claims.

Aspects of the present disclosure are described above with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, such as a service processor, or other programmable data processing apparatus to produce a machine, such that the instructions, which execute via the processor of the computer or other programmable data processing apparatus, performs the method for implementing the functions/acts specified in the flowchart and/or block diagram block or blocks.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure not be limited to the particular embodiments disclosed for carrying out this disclosure, but that the disclosure will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the disclosure. As used herein, the singular forms "a", "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

We claim:

1. A test apparatus for evaporation or boiloff flow measuring to determine thermal performance of a test specimen, comprising:
   a sealable chamber comprising a vacuum chamber can and a vacuum chamber lid that is selectably sealed to an upper opening of the vacuum chamber can;
   a cold mass assembly attached to a bottom side of the vacuum chamber lid and locatable within the sealable chamber and comprising:
      a guard vessel having a guard chamber to receive a first liquid fluid and a bottom surface to contact an upper side of a test specimen, and
      a test vessel having a test chamber to receive a second liquid fluid and encompassed on one side by a center portion of the bottom surface shared with the guard vessel, the test vessel further comprising a lateral wall assembly closed by a vessel top, the lateral wall assembly comprising an outer wall and an inner wall having opposing surfaces that define a thermal break including a condensable vapor pocket to inhibit heat transfer through the lateral wall from the guard vessel to the test vessel;
   a first liquid passage in communication with the guard vessel to supply the first liquid fluid and to vent evaporation or boiloff from the first liquid fluid;
   a second liquid in communication with the test vessel to supply the second liquid fluid and to vent evaporation or boiloff from the second liquid fluid; and
   a warm boundary temperature surface in thermal communication with a lower surface of the test specimen, wherein the upper surface of the test specimen during testing is colder than the lower surface and thus deemed a cold side and a warm side respectively,
   wherein the first liquid in the guard vessel is maintained at a level higher than the top of the test vessel encompassing the lateral wall assembly and the vessel top of the test vessel creating a steady-state thermal isolation enabling direct measurement of flow of heat.

2. The test apparatus of claim 1, further comprising a cold edge guard that laterally encompasses a space for the test specimen between the bottom surface and the warm boundary temperature surface.

3. The test apparatus of claim 1, further comprising:
   a test specimen stand to support the warm boundary temperature surface and to space the test specimen from the bottom of the sealable chamber; and
   an insulative material that fills the test specimen stand to dampen ambient vibrations and mitigate atmospheric conditions outside of the sealable chamber.

4. The test apparatus of claim 1, wherein the sealable chamber comprises a lid and a vacuum can, the test apparatus further comprising:
   more than one compliance rod having a low thermal conductivity and is adjustable to suspend the cold mass assembly from the lid for a range of test specimen thicknesses at a selected amount of compression force.

5. The test apparatus of claim 1, further comprising a test system that operates a test procedure for heat flux values from below 0.5 $W/m^2$ up to approximately 500 $W/m^2$ and effective thermal conductivity values from below 0.05 mW/m-K up to approximately 500 mW/m-K.

6. The test apparatus of claim 1, further comprising:
   one or more temperature sensors positioned in the sealable chamber;
   one or more sealable ports in the sealable chamber; and one or more electrical wires comprising temperature sensors having adequate length to reduce heat leakage into the cold mass assembly.

7. The test apparatus of claim 6, wherein the temperature sensors are silicon diodes, resistance thermometers, or thermocouples from a selected type E, K, or T of diameter size less than 28 gage and having a length inside of the sealable chamber of at least one meter.

8. The test apparatus of claim 1, wherein the lateral wall assembly comprises the outer wall seal welded to the inner wall to seal the thermal break and to establish a void space.

9. The test apparatus of claim 1, wherein the test vessel liquid level is allowed to diminish to a level in a range between 1 percent and 99 percent.

10. The test apparatus of claim 9, wherein the one or more temperature sensors are positioned on the surfaces of the guard or test vessels to indicate the respective liquid levels inside the chambers during the cooling, filling, or boiloff operations.

11. The test apparatus of claim 1, wherein the warm boundary temperature surface is further comprised of a warm boundary temperature control system consisting of a heater plate assembly in physical contact with the lower surface of the test specimen.

12. The test apparatus of claim 11, wherein the heater plate assembly is comprised of an electrical heater that is sandwiched between an upper conductive plate and a lower conductive plate.

13. The test apparatus of claim 11, wherein the heater plate assembly is comprised of an electrical heater that is sandwiched between an upper conductive plate and a lower conductive plate and includes one or more temperature sensors imbedded within the upper conductive plate to provide data output for control of the warm boundary temperature.

* * * * *